US007364737B2

(12) United States Patent
Burton et al.

(10) Patent No.: US 7,364,737 B2
(45) Date of Patent: Apr. 29, 2008

(54) HUMAN NEUTRALIZING MONOCLONAL ANTIBODIES TO RESPIRATORY SYNCYTIAL VIRUS

(75) Inventors: Dennis R. Burton, La Jolla, CA (US); Carlos F. Barbas, III, San Diego, CA (US); Robert M. Chanock, Bethesda, MD (US); Brian R. Murphy, Bethesda, MD (US); James E. Crowe, Jr., Chevy Chase, MD (US)

(73) Assignee: The Scripps Research Institute, La Jolla, CA (US)

( * ) Notice: Subject to any disclaimer, the term of this patent is extended or adjusted under 35 U.S.C. 154(b) by 223 days.

(21) Appl. No.: 10/768,952

(22) Filed: Jan. 29, 2004

(65) Prior Publication Data

US 2004/0234528 A1 Nov. 25, 2004

Related U.S. Application Data

(60) Continuation of application No. 08/920,100, filed on Aug. 26, 1997, now Pat. No. 6,685,942, which is a division of application No. 08/162,102, filed on Dec. 10, 1993, now Pat. No. 5,762,905, which is a continuation-in-part of application No. 07/945,515, filed as application No. PCT/US93/08786 on Sep. 16, 1993, now abandoned.

(51) Int. Cl.
*A61K 39/395* (2006.01)
*A61K 39/42* (2006.01)
*C07K 16/08* (2006.01)

(52) U.S. Cl. .............................. 424/159.1; 424/133.1; 424/142.1; 424/147.1; 424/800; 424/801; 424/141.1; 424/809; 424/130.1; 530/388.3; 530/388.2; 530/389.4; 530/387.3; 530/388.15; 530/866; 530/387.1; 530/867

(58) Field of Classification Search ..................... None
See application file for complete search history.

(56) References Cited

U.S. PATENT DOCUMENTS

| | | | |
|---|---|---|---|
| 4,800,078 | A | 1/1989 | Prince et al. |
| 4,994,269 | A | 2/1991 | Collins et al. |
| 5,049,388 | A | 9/1991 | Knight et al. |
| 5,223,409 | A | 6/1993 | Ladner et al. |
| 5,403,484 | A | 4/1995 | Ladner et al. |
| 5,639,853 | A | 6/1997 | Paradise et al. |
| 5,658,569 | A | 8/1997 | Osther et al. |
| 5,824,307 | A | 10/1998 | Johnson |

FOREIGN PATENT DOCUMENTS

| | | |
|---|---|---|
| WO | WO 91/16074 | 10/1991 |
| WO | WO 92/01473 | 2/1992 |
| WO | WO 92/04381 | 3/1992 |

OTHER PUBLICATIONS

Barbas et al., PNAS USA, 89:10164-10168, 1992.

Beeler et al., J. Virol., 63:2941-2950, 1989.

Burton, et al., "A large array of human monoclonal antibodies to type 1 human immunodeficiency virus from combinatorial libraries of asymptomatic serpositive individuals", *Proc. Natl. Acad. Sci.*, vol. 88, pp. 10134-10137, Nov. 1991.

Barbas, et al., "Assembly of combinatorial antibody libraries on phage surfaces: the gene III site", *Proc. Natl. Acad. Sci.*, vol. 88, pp. 7978-7982, Sep. 1991.

Okamoto, et al., "Effect of Breast Feeding on the Development of Anti-Idiotype Antibody Response to F Glycoprotein of Respiratory Syncytial Virus in Infant Mice after Post-Partum Maternal Immunization", *The Journal of Immunology*, vol. 142, No. 7, pp. 2507-2512, Apr. 1, 1989.

Tempest, et al., "Reshaping a Human Monoclonal Antibody to Inhibit Human Respiratory Syncytial Virus Infection In Vivo", *Biotechnology*, vol. 9, pp. 266-271, Mar. 1991.

*Primary Examiner*—Ronald B. Schwadron
(74) *Attorney, Agent, or Firm*—Catalyst Law Group, APC; David M. Kohn

(57) ABSTRACT

Human monoclonal antibodies and fragments thereof which bind, neutralize and provide passive immunotherapy to respiratory syncytial virus (RSV) antigenic subgroups A and B are disclosed. Also disclosed are diagnostic and immunotherapeutic methods of using the monoclonal antibodies as well as cell line producing the monoclonal antibodies.

16 Claims, 6 Drawing Sheets

| Clone | FR1 | CDR1 | FR2 | CDR2 |
|---|---|---|---|---|
| rsv6/11/21/22/23H | QVKLLEQSGGGLVQPGGSLRLSCAVSGVTFS | AYAWS | WVRQAPGKGLEWVS | GISGSGDSTDYADSVKG |
| rsv13/19H | QVKLLEESGGGLVRLAGSLRLSCAASGTTLS | GYTMH | WVRQAPGKGLEWVS | SITGGSNFINYSDSVKG |
| rsv6/11/21/22L | MAELTQSPGTLSLSPGERATLSC | RATQSISSNYLA | WYQQRPGQAPRLLIY | GASNRAT |
| rsv23L | MAELTQSPVTLSVSPGERVALSC | KASQNINDNLA | WYQQKPGQAPRLLIY | GASSRAT |
| rsv13/19L | MAELTQSPSSLSASVGDRVTITC | RATQSVSNFLN | WYQQKPGEAPTLLIY | DASTSQS |

| Clone | FR3 | CDR3 | FR4 |
|---|---|---|---|
| rsv6/11/21/22/23H | RLTISRDNSKNTLYLQMNSLRAEDTAIYYCAS | HLPDYMNLDYTRFFYMDV | WGKGTTVTVSS |
| rsv13/19H | RFTISRDNAKNSLYLQMNSLTAEDTAVYYCAT | APIAPPYFDH | WGQGILVTVSS |
| rsv6/11/21/22L | DIPDRFSGSGSGTDFTLTISRLEPEDFAMYYC | QQYDISPYT | FGQGTKLEIKR |
| rsv23L | GIPDRFSGSGSGTDFTLTIRLEPEDFAVYYC | QQYGGSPYT | FGQGTKLEIKRT |
| rsv13/19L | GVPSRFSCSGSGMDFSLTISSLQPEDLAMYYC | QASINTPL | FGEGTRIDMRRT |

FIG.4

LIGHT CHAIN LINKER:

```
5'... AA  GCT  TAG  GGA  ACC  ATG  GAA  ACC  CCA  GCG
3'... TT  CGA  ATC  CCT  TGG  TAC  CTT  TGG  GGT  CGC
      HindIII            START
                         M    E    T    P    A CAG  CTT  CTC  TTC  CTC  CTG  CTA  CTC  TGG  CTC
      GTC  GAA  GAG  AAG  GAG  GAC  GAT  GAG  ACC  GAG

Q    L    L    F    L    L    L    L    W    L

CCA  GAT  ACC  ACC  GGA  GAA  ATT  C/GAG CTC        ...3'
      GGT  CTA  TGG  TGG  CCT  CTT  TAA  G/CTC GAG        ...5'
                                          (SacI)
      P    D    T    T    G    E    I    Q/E  L           ...C
```

HEAVY CHAIN LINKER:

```
5'... AA  GCT  TAA  CTC  ACC  ATG  GAG  TTT  GGG  CTG
3'... TT  CGA  ATT  GAG  TGG  TAC  CTC  AAA  CCC  GAC
      HindIII              START
                           M    E    F    G    L AGC  TGG  CTT  TTT  CTT  GTG  GCT  ATT  TTA  AAA
      TCG  ACC  GAA  AAA  GAA  CAC  CGA  TAA  AAT  TTT
       S    W    L    F    L    V    A    I    L    K GCT  GTC  CAG  TGT  GAG  GTG  CAG  CTG  CTC  GAG  ...3'
      CGA  CAG  GTC  ACA  CTC  CAC  GTC  GAC  GAG  CTC  ...5'
                                                 XhoI
       G    V    Q    C    E    V    Q    L    L    E   ...C
```

HUMAN NEUTRALIZING MONOCLONAL ANTIBODIES TO RESPIRATORY SYNCYTIAL VIRUS

CROSS REFERENCE TO RELATED APPLICATIONS

This application is a continuation (and claims the benefit of priority under 35 USC 120) of U.S. application Ser. No. 08/920,100, filed Aug. 26, 1997, (now U.S. Pat. No. 6,685,942), which application is a divisional and claims priority to U.S. application Ser. No. 08/162,102, filed Dec. 10, 1993, (now U.S. Pat. No. 5,762,905), which claims priority to and is a continuation-in-part of U.S. application Ser. No. 07/945,515, filed Sep. 16, 1992, now abandoned, and is a 371 and claims priority of PCT Application No. PCT/US93/08786, Sep. 16, 1993. The disclosures of the prior applications are considered part of (and are incorporated by reference in) the disclosure of this application.

BACKGROUND OF THE INVENTION

1. Field of the Invention

This invention relates generally to the field of immunology and specifically to human monoclonal antibodies which bind and neutralize respiratory syncytial virus (RSV).

2. Description of Related Art

RSV is the major viral-pathogen of the pediatric respiratory tract and has been identified as a leading cause of pneumonia and bronchiolitis. In the United States alone, there is a relatively large population of infants and children, about 100,000 to 200,000, at high risk of developing severe or fatal RSV illness. The high risk population includes infants and children with bronchopulmonary dysplasia, congenital heart disease, cystic fibrosis, cancer or various forms of immunodeficiency, as well as adults immunosuppressed prior to bone marrow transplantation, for example (McIntosh and Chanock (1990) Virology, 2nd edn. (Fields and Knipe, eds) Raven Press, Ltd., New York, pp. 1045-1072).

Several lines of evidence indicate that antibodies mediate resistance to RSV infection and illness. First, there is a correlation between levels of maternal IgG antibodies to RSV and the resistance of infants to infection during the first months of life when the risk of severe disease is greatest (Ogilvie, et al., *J. Med. Virol.*, 7:263, 1981). Second, pooled human IgG containing a high level of RSV neutralizing antibodies or appropriate murine monoclonal antibodies that neutralize RSV efficiently can protect small animals from pulmonary infection when administered prophylactically and can reduce the titer of virus in the lungs of small animals and experimental primates at the height of RSV infection when administered therapeutically (Walsh, et al., *Infection and Immunity*, 43:756, 1984; Prince, et al., *J. Virol.*, 55:517, 1985; Prince, et al., *Virus Research*, 3:193, 1985; Prince, et al., *J. Virol.*, 63:1851, 1987; Hemming, et al., *J. Inf. Dis.*, 152:1083, 1985). Third, a clinical study of pooled human IgG containing a high titer of RSV neutralizing antibodies has provided preliminary indications that these antibodies can exert a therapeutic effect on serious RSV disease in infants and young children (Hemming, et al., *Antimicrob. Agnts. Chemotherap.*, 31:1882, 1987). Given this evidence, there is considerable interest in developing neutralizing antibodies to RSV for immunoprophylaxis and therapy for protecting infants at high risk of serious disease and for therapy in cases of serious RSV lower respiratory tract infection.

At present, there is no RSV vaccine available. The strategy currently being evaluated for prophylactic efficacy entails periodic intravenous inoculation of human IgG prepared from pooled plasma. Because of the large quantity of globulin required (1 to 2 gm per kg) and the need to administer this material intravenously in the clinic or hospital over a 2 to 4 hour interval every month during the fall, winter and early spring, this strategy is not very practical.

The main neutralization antigens on the surface of the RSV virion are the major glycoproteins F (viral fusion) and G (attachment). Monospecific antiserum prepared against immunoaffinity purified F or G glycoprotein neutralizes RSV with high efficiency (Walsh, et al., *J. Gen. Microbiol.*, 67:505. 1986). The antiserum to F, but not G, also inhibits fusion of RSV-infected cells to neighboring uninfected cells.

There is a need to develop human RSV antibody preparations with greater specific activity than the pooled human plasma preparations. A potentially effective solution to this problem would be the utilization of human monoclonal antibodies to RSV. RSV-specific monoclonal antibody, in contrast to polyclonal antisera, contains, by its very nature, a higher concentration of specific antibody. Therefore, the use of monoclonal antibody would decrease the amount of globulin required for prophylaxis or therapy by several orders of magnitude. As a consequence, an effective dose of monoclonal antibody could be administered intramuscularly (IM), rather than intravenously (IV) over a long period of time. Prophylaxis of infants at high risk could be accomplished IM at home, avoiding the need for hospital treatment for IV administration of antibodies. A reduction in the amount of globulin needed for therapy should also make it possible to treat patients with early mild RSV lower respiratory tract disease by administering antibodies IM in order to prevent hospitalization. In addition, aerosol therapy becomes feasible due to the increased specific activity of monoclonal antibodies, and accompanying decrease in therapeutic concentration necessary, coupled with increased therapeutic efficacy of such antibodies when introduced directly into the lungs. In fact, for aerosol application, $F(ab')_2$ fragments of the RSV monoclonal antibodies are sufficient. Useful antibody preparations should also be capable of neutralizing a wide range of RSV isolates, including those of both antigenic subgroups A and B. The two subgroups, A and B, circulate simultaneously in the population in varying proportion at different times and are estimated to be 50% related in the F glycoprotein and 1-5% related in the G glycoprotein (McIntosh and Chanock, supra).

During the last several years, the efficiency of topical immunotherapy for RSV infection has been increased by two modifications of previous methodology. First, a mixture of RSV F murine monoclonal antibodies directed at the major conserved neutralization epitopes on this glycoprotein was shown effective in topical immunotherapy of RSV infection in the cotton rat. Second, delivery of RSV polyclonal antibodies directly into the lungs in a small particle aerosol (less than 2 μm) was also effective therapeutically. The use of monoclonal antibodies should decrease the amount of IgG required for therapy by at least 2 orders of magnitude. In other studies in cotton rats, parainfluenza virus type 3 (PIV3) antibodies were also shown to be therapeutic when administered directly into the respiratory tract. The usefulness of topical immunotherapy is not limited to RSV. This approach likely will be effective for other respiratory viral pathogens whose pathogenic effects are also limited to the cells that line the lumen of the lower respiratory tract.

SUMMARY OF THE INVENTION

The present invention provides human monoclonal antibodies which bind and neutralize antigenic subgroups A and B of respiratory syncytial virus (RSV) and cell lines which produce these monoclonal antibodies. Also provided are amino acid sequences which confer neutralization function to the paratope of these monoclonal antibodies and which can be used immunogenically to identify other antibodies that specifically bind and neutralize RSV. The monoclonal antibodies of the invention find particular utility as reagents for the diagnosis and immunotherapy of RSV disease.

A major advantage of the monoclonal antibodies of the invention derives from the fact that they are encoded by a human polynucleotide sequence. Thus, in vivo use of the monoclonal antibodies of the invention for diagnosis and immunotherapy of RSV disease greatly reduces the problems of significant host immune response to the passively administered antibodies which is a problem commonly encountered when monoclonal antibodies of xenogeneic or chimeric derivation are utilized.

The antibodies of the invention are particularly efficacious in ameliorating RSV disease when administered directly to the lungs. This was surprisingly found to be true of Fab fragments. Topical delivery of RSV antibodies directly into the lungs has a major advantage over parenteral administration of antibodies for therapy of RSV disease. Antibodies delivered by the former route are approximately 80 to 160 times more effective in therapy, thereby decreasing the amount of antibodies required for therapy by a factor of 80 to 160. A further reduction in amount of antibodies required for therapy can be achieved by using human monoclonal antibodies or "humanized" murine monoclonal antibodies such that the amount required for therapy is reduced by an additional factor of 25 to 50. This means that the total amount of antibodies required for therapy by parenteral treatment can be reduced by a factor of 2000 to 8000 when monoclonal antibodies are administered directly into the lungs for treatment of RSV infection. The ability to utilize Fab fragments in vivo for respiratory viral infections provides significant advantages over the use of whole antibody molecules such as: (1) greater tissue penetration; (2) avoidance of effector functions associated with Fc, such as inflammation; and (3) rapid clearance.

The in vivo therapeutic effectiveness of Fab fragments in treating respiratory viral infection is surprising and unexpected in view of the fact that: (1) Fab's are non-covalent and can only attach to a single site, thereby precluding cross linking on separate virus particles, which is commonly thought to be necessary for viral neutralization; and (2) the Fc portion is thought to be needed in viral clearance in order to effect the complement cascade and antibody dependent cell cytotoxicity (ADCC). In view of the unexpected finding that pulmonary administration of Fab fragments which specifically bind RSV could be used effectively to ameliorate RSV infection, it is now possible to broadly apply this teaching to any viral infection where the in vivo viral growth occurs at the lumenal surface of the respiratory tract.

BRIEF DESCRIPTION OF THE DRAWINGS

FIG. 4 shows the heavy and light chain variable domains of clones 13, 19, 11, and 4 other randomly chosen clones; and (SEQ ID Nos:21-25, respectively).

DETAILED DESCRIPTION OF THE INVENTION

Figure 1:
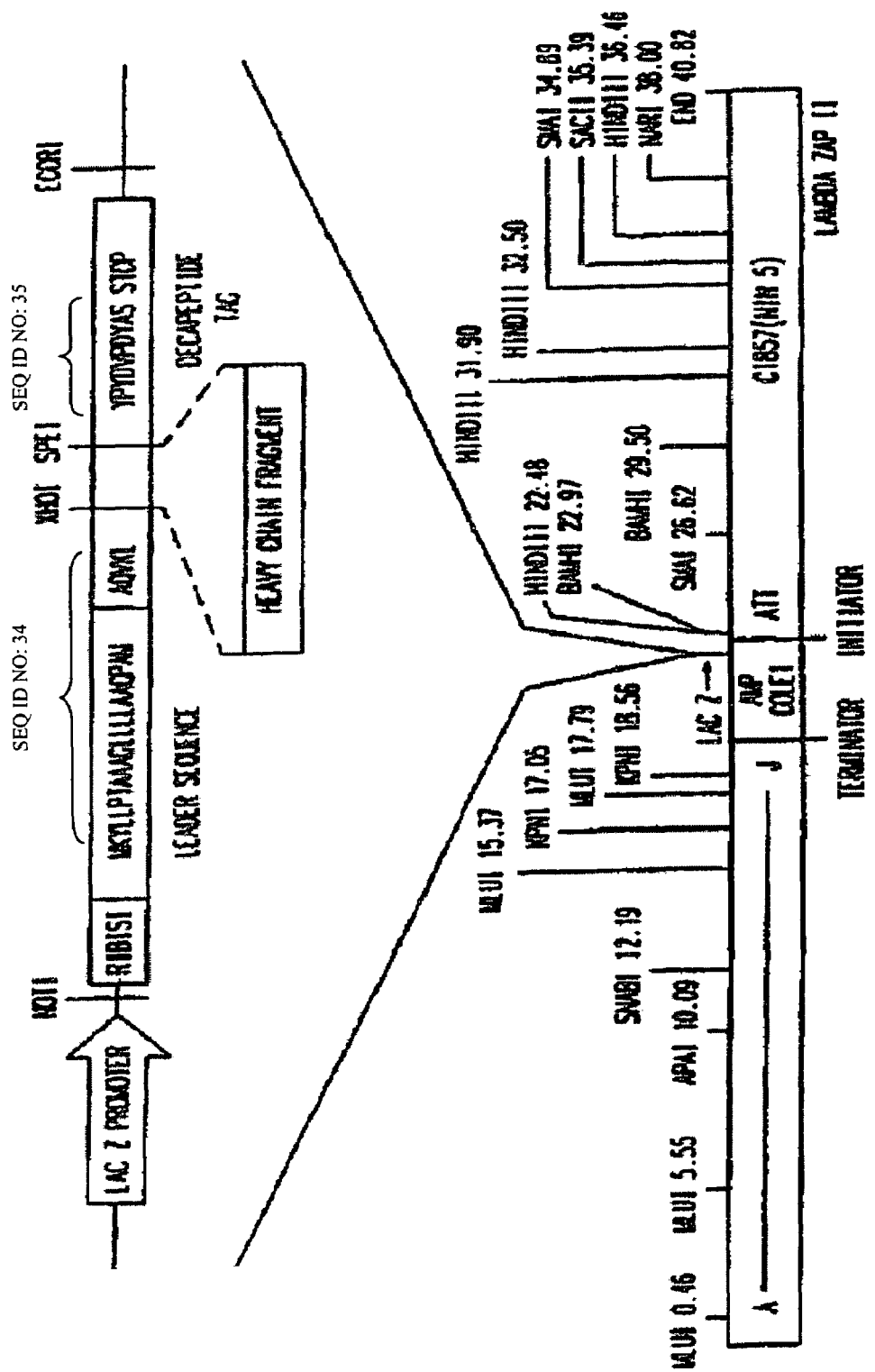
FIG. 1 shows the Lambda Hc2 expression vector (SEQ ID NO:34).

The present invention relates to human monoclonal antibodies which are specific for, and neutralize respiratory syncytial virus (RSV) antigenic subgroups A and B. In a preferred embodiment of the invention, human monoclonal antibodies are disclosed which are capable of binding epitopic polypeptide sequences in glycoprotein F of RSV. Also disclosed is an amino acid sequence which confers neutralization of RSV when the virus is bound by these antibodies. This specificity enables the human monoclonal antibody, and human monoclonal antibodies with like specificity, to be used in the diagnosis and immunotherapy of RSV disease.

The term "RSV disease" means any disease caused, directly or indirectly, by RSV as well as diseases which predispose a patient to infection by RSV. Examples of diseases falling into the former category include pneumonia and bronchiolitis. Diseases in the latter category (i.e., those which place the patient at risk of severe RSV infection) include cystic fibrosis, congenital heart diseases, cancer and, generally, any condition that causes a state of a immunosuppression or decreased function of the immune system such as patients who receive organ transplants and premature infants.

In one aspect, the present invention is directed to combinatorially derived human monoclonal antibodies which are reactive with a RSV neutralization site and cell lines which produce such antibodies. The isolation of cell lines producing monoclonal antibodies of the invention can be accomplished using routine screening techniques which permit determination of the elementary reaction pattern of the monoclonal antibody of interest. Thus, if a human monoclonal antibody being tested binds and neutralizes members of antigenic subgroups A and B of RSV, then the human monoclonal antibody being tested and the human monoclonal antibody produced by the cell lines of the invention are equivalent.

It is also possible to determine, without undue experimentation, if a human monoclonal antibody has the same specificity as a human monoclonal antibody of the invention by ascertaining whether the former prevents the latter from binding to RSV. If the human monoclonal antibody being tested competes with the human monoclonal antibody of the invention, as shown by a decrease in binding by the human monoclonal antibody of the invention, then it is likely that the two monoclonal antibodies bind to the same, or a closely related, epitope. Still another way to determine whether a human monoclonal antibody has the specificity of a human monoclonal antibody of the invention is to pre-incubate the human monoclonal antibody of the invention with RSV with which it is normally reactive, and then add the human monoclonal antibody being tested to determine if the human monoclonal antibody being tested is inhibited in its ability to bind RSV. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out utilizing RSV and determining whether the monoclonal antibody neutralizes RSV.

By using the human monoclonal antibodies of the invention, it is now possible to produce anti-idiotypic antibodies which can be used to screen human monoclonal antibodies to identify whether the antibody has the same binding specificity as a human monoclonal antibody of the invention and also used for active immunization (Herlyn, et al., Science, 232:100, 1986). Such anti-idiotypic antibodies can be produced using well-known hybridoma techniques (Kohler and Milstein, Nature, 256:495, 1975). An anti-idiotypic antibody is an antibody which recognizes unique determinants present on the human monoclonal antibody produced by the cell line of interest. These determinants are located in the hypervariable region of the antibody. It is this region which binds to a given epitope and, thus, is responsible for the specificity of the antibody. An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the human monoclonal antibody of the invention produced by a cell line which was used to immunize the second animal, it is now possible to identify other clones with the same idiotype as the antibody of the hybridoma used for immunization. Idiotypic identity between human monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody. Thus, the anti-idiotypic monoclonal antibody can be used for immunization, since the anti-idiotype monoclonal antibody binding domain effectively acts as an antigen.

The term "antibody" as used in this invention includes intact molecules as well as fragments thereof, such as Fab and $F(ab')_2$, which are capable of binding the epitopic determinant. In the present invention Fab fragments are preferred. Fabs offer several advantages over $F(ab')_2$s and whole immunoglobulin molecules as a therapeutic modality. First, because Fabs have only one binding site for their cognate antigen, the formation of immune complexes is precluded, whereas such complexes can be generated when divalent $F(ab')_2$s and whole immunoglobulin molecules encounter their target antigen. This is of some importance because immune complex deposition in tissues can produce adverse inflammatory reactions. Second, since Fabs lack an Fc region they cannot trigger adverse inflammatory reactions that are activated by Fc, such as initiation of the complement cascade. Third, the tissue penetration of the small Fab molecule is likely to be much better than that of the larger whole antibody. Fourth, Fabs can be produced easily and inexpensively in bacteria, such as E. coli, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression cells in culture with the attendant problems of serum-containing culture medium. In contrast, production of Fabs in E. coli eliminates these difficulties and makes it possible to produce these antibody fragments in large fermenters which are less expensive than cell culture-derived products.

In addition to Fabs, smaller antibody fragments and epitope-binding peptides having binding specificity for at least one epitope of RSV, preferably on glycoprotein F of RSV, are also contemplated by the present invention and can also be used to neutralize the virus. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escheria coli,*" Nature 341: 644-646, disclose a method for screening to obtain an antibody heavy chain variable region (VH single domain antibody) with sufficient affinity for its target epitope to bind thereto in isolate form.

The monoclonal antibodies of the invention are suited for in vitro for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of RSV. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

For purposes of the invention, RSV may be detected by the monoclonal antibodies of the invention when present in biological fluids and tissues. Any sample containing a detectable amount of RSV can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a human monoclonal antibody of the invention which is, or can be, detectably labelled. The kit may also have containers containing buffer(s) and/or a container comprising a reporter-means, such as a biotin-binding protein, such as avidin or streptavidin, bound to a reporter molecule, such as an enzymatic, or fluorescent label.

In using the human monoclonal antibodies of the invention for the in vivo detection of antigen, the detectably labeled monoclonal antibody is given in a dose which is diagnostically effective. The term "diagnostically effective" means that the amount of detectably labeled human monoclonal antibody is administered in sufficient quantity to enable detection of the site having the RSV antigen for which the monoclonal antibodies are specific.

The concentration of detectably labeled human monoclonal antibody which is administered should be sufficient such that the binding to RSV is detectable compared to the background. Further, it is desirable that the detectably labeled monoclonal antibody be rapidly cleared from the circulatory system in order to give the best target-to-background signal ratio.

As a rule, the dosage of detectably labeled human monoclonal antibody for in vivo diagnosis will vary depending on such factors as age, sex, and extent of disease of the individual. The dosage of human monoclonal antibody can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on whether multiple injections are given, tissue, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 keV range, which may be readily detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, 52Cr, and 56Fe.

The human monoclonal antibodies of the invention can be used in vitro and in vivo to monitor the course of RSV disease therapy. Thus, for example, by measuring the increase or decrease in the number of cells infected with RSV or changes in the concentration of RSV present in the body or in various body fluids, it would be possible to determine whether a particular therapeutic regimen aimed at ameliorating the RSV disease is effective.

The human monoclonal antibodies can also be used immunotherapeutically for RSV disease. The term "immunotherapeutically" or "immunotherapy" as used herein in conjunction with the monoclonal antibodies of the invention denotes both prophylactic as well as therapeutic administration. Thus, the monoclonal antibodies can be administered to high-risk patients in order to lessen the likelihood and/or severity of RSV disease or administered to patients already evidencing active RSV infection.

In the present invention the surprising discovery that Fab fragments which neutralize RSV in vitro can be used therapeutically to treat RSV infection in vivo suggests that a similar approach can be used for other pulmonary viral infections. Thus, in a broader sense the invention embraces the use of Fab fragments which neutralize a virus to treat infection in vivo and caused by the virus, wherein the growth of the virus is limited to the lumenal surface of the respiratory tract of the host. Such viruses include influenza virus, parainfluenza virus, rhinovirus, and coronavirus, as well as RSV, as shown in the Examples herein. The identification of Fab fragments specific for other pulmonary viruses can be accomplished using routine neutralization assays well known in the art without resort to undue experimentation.

The dosage ranges for the administration of the monoclonal antibodies of the invention are those large enough to produce the desired effect in which the symptoms of the RSV disease are ameliorated or the likelihood of infection is decreased. The dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The dosage can be adjusted by the individual physician in the event of any complication. Dosage can vary from about 0.01 mg/kg to about 300 mg/kg, preferably from about 0.1 mg/kg to about 200 mg/kg, most preferably from about 0.2 mg/kg to about 20 mg/kg, in one or more dose administrations daily, for one or several days. Preferred is administration of the antibody for 2 to 5 or more consecutive days in order to avoid "rebound" of virus replication from occurring.

The human monoclonal antibodies of the invention can be administered parenterally by injection or by gradual infusion over time. The human monoclonal antibodies of the invention can be administered intravenously, intraperitoneally, intramuscularly, subcutaneously, intracavity, or transdermally. When used therapeutically, a preferred route of administration of the human monoclonal antibodies of the invention is by pulmonary aerosol. Techniques for preparing aerosol delivery systems containing the antibody of the invention are well known those of skill in the art. Generally, such systems should utilize components which will not significantly impair the biological properties of the antibody, such as the paratope binding capacity (see, for example, Sciarra and Cutie, Aerosols, in *Remington Pharmaceutical Sciences*, 18th edition, 1990, pp 1694-1712; incorporated by reference). Those of skill in the art can readily determine the various parameters and conditions for producing antibody aerosols without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer' dextrose, dextrose and sodium chloride, lactated Ringer's, or fixed oils. Intravenous vehicles include fluid and nutrient replenishers, electrolyte replenishers (such as those based on Ringer' dextrose), and the like. Preservatives and other additives may also be present such as, for example, antimicrobials, anti-oxidants, chelating agents, and inert gases and the like.

The invention also relates to a method for preparing a medicament or pharmaceutical composition comprising the human monoclonal antibodies of the invention, the medicament being used for immunotherapy of RSV disease.

A preferred embodiment of the invention relates to human monoclonal antibodies whose heavy chains comprise in CDR3 the polypeptides APIAPPYFDH (SEQ.I.D.NO. 1), HLPDYWNLDYTRFFYYMDV (SEQ.I.D.NO. 2), and conservative variations of these peptides. Also encompassed by the present invention are certain amino acid sequences that bind to epitopic sequences in glycoprotein F of RSV and confer neutralization of RSV when bound thereto. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also neutralize RSV. Analogously, another preferred embodiment of the invention relates to polynucleotides which encode the above noted heavy chain polypeptide and to polynucleotide sequences which are complementary to these polynucleotide sequences. Complementary polynucleotide sequences include those sequences which hybridize to the polynucleotide sequences of the invention under stringent hybridization conditions.

A preferred vector of the present invention is a recombinant DNA (rDNA) molecule containing a nucleotide sequence that codes for and is capable of expressing a fusion polypeptide containing, in the direction of amino- to carboxy-terminus, (1) a prokaryotic secretion signal domain, (2) a heterologous polypeptide, and (3) a filamentous phage membrane anchor domain. The vector includes DNA expression control sequences for expressing the fusion polypeptide, preferably prokaryotic control sequences.

The filamentous phage membrane anchor is preferably a domain of the cpIII or cpVIII coat protein capable of associating with the matrix of a filamentous phage particle, thereby incorporating the fusion polypeptide onto the phage surface.

The secretion signal is a leader peptide domain of a protein that targets the protein to the periplasmic membrane of gram negative bacteria. A preferred secretion signal is a pelB secretion signal. The predicted amino acid residue sequences of the secretion signal domain from two pelB gene product variants from *Erwinia carotova* are described in Lei, et al. (Nature, 331:543-546, 1988). The leader sequence of the pelB protein has previously been used as a secretion signal for fusion proteins (Better, et al., *Science*, 240:1041-1043, 1988; Sastry, et al., *Proc. Natl. Acad. Sci. USA*, 86:5728-5732, 1989; and Mullinax, et al., *Proc. Natl. Acad. Sci. USA*, 87:8095-8099, 1990). Amino acid residue sequences for other secretion signal polypeptide domains from *E. coli* useful in this invention can be found in Oliver, In Neidhard, F. C. (ed). *Escherichia coli* and *Salmonella Typhimurium*, American Society for Microbiology, Washington, D.C., 1:56-69 (1987).

Preferred membrane anchors for the vector are obtainable from filamentous phage M13, f1, fd, and equivalent filamentous phage. Preferred membrane anchor domains are found in the coat proteins encoded by gene III and gene VIII. The membrane anchor domain of a filamentous phage coat protein is a portion of the carboxy terminal region of the coat protein and includes a region of hydrophobic amino acid residues for spanning a lipid bilayer membrane, and a region of charged amino acid residues normally found at the cytoplasmic face of the membrane and extending away from the membrane. In the phage f1, gene VIII coat protein' membrane spanning region comprises residue Trp-26 through Lys-40, and the cytoplasmic region comprises the carboxy-terminal 11 residues from 41 to 52 (Ohkawa, et al., J. Biol. Chem., 256:9951-9958, 1981). An exemplary membrane anchor would consist of residues 26 to 40 of cpVIII. Thus, the amino acid residue sequence of a preferred membrane anchor domain is derived from the M13 filamentous phage gene VIII coat protein (also designated cpVIII or CP 8). Gene VIII coat protein is present on a mature filamentous phage over the majority of the phage particle with typically about 2500 to 3000 copies of the coat protein.

In addition, the amino acid residue sequence of another preferred membrane anchor domain is derived from the M13 filamentous phage gene III coat protein (also designated cpIII). Gene III coat protein is present on a mature filamentous phage at one end of the phage particle with typically about 4 to 6 copies of the coat protein. For detailed descriptions of the structure of filamentous phage particles, their coat proteins and particle assembly, see the reviews by Rached, et al. (Microbiol. Rev., 50:401-427 1986; and Model, et al., in "The Bacteriophages: Vol. 2", R. Calendar, ed. Plenum Publishing Co., pp. 375-456, 1988).

DNA expression control sequences comprise a set of DNA expression signals for expressing a structural gene product and include both 5' and 3' elements, as is well known, operatively linked to the cistron such that the cistron is able to express a structural gene product. The 5' control sequences define a promoter for initiating transcription and a ribosome binding site operatively linked at the 5' terminus of the upstream translatable DNA sequence.

To achieve high levels of gene expression in E. coli, it is necessary to use not only strong promoters to generate large quantities of mRNA, but also ribosome binding sites to ensure that the mRNA is efficiently translated. In E. coli, the ribosome binding site includes an initiation codon (AUG) and a sequence 3-9 nucleotides long located 3-11 nucleotides upstream from the initiation codon (Shine, et al., Nature, 254:34, 1975). The sequence, AGGAGGU, which is called the Shine-Dalgarno (SD) sequence, is complementary to the 3' end of E. coli 16S rRNA. Binding of the ribosome to mRNA and the sequence at the 3' end of the mRNA can be affected by several factors:

(i) The degree of complementarity between the SD sequence and 3 end of the 16S rRNA.

(ii) The spacing and possibly the DNA sequence lying between the SD sequence and the AUG (Roberts, et al., Proc. Natl. Acad. Sci. USA, 76:760, 1979a; Roberts, et al., Proc. Natl. Acad. Sci. USA, 76:5596, 1979b; Guarente, et al., Science, 209:1428, 1980; and Guarente, et al., Cell, 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., Annu. Rev. Microbiol., 35:365, 1981). Leader sequences have been shown to influence translation dramatically (Roberts, et al., 1979 a, b supra).

(iii) The nucleotide sequence following the AUG, which affects ribosome binding (Taniguchi, et al., J. Mol. Biol., 118:533, 1978).

The 3' control sequences define at least one termination (stop) codon in frame with and operatively linked to the heterologous fusion polypeptide.

In preferred embodiments, the vector utilized includes a prokaryotic origin of replication or replicon, i.e., a DNA sequence having the ability to direct autonomous replication and maintenance of the recombinant DNA molecule extra chromosomally in a prokaryotic host cell, such as a bacterial host cell, transformed therewith. Such origins of replication are well known in the art. Preferred origins of replication are those that are efficient in the host organism. A preferred host cell is E. coli. For use of a vector in E. coli, a preferred origin of replication is ColE1 found in pBR322 and a variety of other common plasmids. Also preferred is the p15A origin of replication found on pACYC and its derivatives. The ColE1 and p15A replicon have been extensively utilized in molecular biology, are available on a variety of plasmids and are described at least by Sambrook, et al., Molecular Cloning: a Laboratory Manual, 2nd edition, Cold Spring Harbor Laboratory Press, 1989).

The ColE1 and p15A replicons are particularly preferred for use in the present invention because they each have the ability to direct the replication of plasmid in E. coli while the other replicon is present in a second plasmid in the same E. coli cell. In other words, ColE1 and p15A are non-interfering replicons that allow the maintenance of two plasmids in the same host (see, for example, Sambrook, et al., supra, at pages 1.3-1.4). This feature is particularly important in the present invention because a single host cell permissive for phage replication must support the independent and simultaneous replication of two separate vectors, namely the vector for expressing a heterologous fusion polypeptide and the vector for expressing a heterodimeric receptor, in this instance a monoclonal antibody which binds and neutralizes RSV.

In addition, those embodiments that include a prokaryotic replicon also include a gene whose expression confers a selective advantage, such as drug resistance, to a bacterial host transformed therewith. Typical bacterial drug resistance genes are those that confer resistance to ampicillin, tetracycline, neomycin/kanamycin or cholamphenicol. Vectors typically also contain convenient restriction sites for insertion of translatable DNA sequences. Exemplary vectors are the plasmids pUC8; pUC9, pBR322, and pBR329 available from BioRad Laboratories, (Richmond, Calif.) and pPL and pKK223 available from Pharmacia, (Piscataway, N.J.).

A vector for expression of heterodimeric receptor, such as the monoclonal antibody of the invention, on the surface of a filamentous phage particle is a recombinant DNA (rDNA) molecule adapted for receiving and expressing translatable first and second DNA sequences in the form of first and second receptor polypeptides wherein one of the receptor polypeptides is fused to a filamentous phage coat protein membrane anchor. That is, at least one of the receptor polypeptides is a fusion polypeptide containing a filamentous phage membrane anchor domain and a prokaryotic secretion signal domain.

A DNA expression vector for expressing a heterodimeric receptor provides a system for independently cloning (inserting) the two translatable DNA sequences into two separate cassettes present in the vector, to form two separate cistrons for expressing the first and second polypeptides of a heterodimeric receptor, or the ligand binding portions of the polypeptides that comprise a heterodimeric receptor. The DNA expression vector for expressing two cistrons is referred to as a dicistronic expression vector.

The vector comprises a first cassette that includes upstream and downstream translatable DNA sequences operatively linked via a sequence of nucleotides adapted for directional ligation to an insert DNA. The upstream translatable sequence encodes the secretion signal as defined herein. The downstream translatable sequence encodes the filamentous phage membrane anchor as defined herein. The cassette preferably includes DNA expression control sequences for expressing the receptor polypeptide that is produced when an insert translatable DNA sequence (insert DNA) is directionally inserted into the cassette via the sequence of nucleotides adapted for directional ligation. The filamentous phage membrane anchor is preferably a domain of the cpIII or cpVIII coat protein capable of binding the matrix of a filamentous phage particle, thereby incorporating the fusion polypeptide onto the phage surface.

The receptor expressing vector also contains a second cassette for expressing a second receptor polypeptide. The second cassette includes a second translatable DNA sequence that encodes a secretion signal, as defined herein, operatively linked at its 3' terminus via a sequence of nucleotides adapted for directional ligation to a downstream DNA sequence of the vector that typically defines at least one stop codon in the reading frame of the cassette. The second translatable DNA sequence is operatively linked at its 5' terminus to DNA expression control sequences forming the 5' elements. The second cassette is capable, upon insertion of a translatable DNA sequence (insert DNA), of expressing the second fusion polypeptide comprising a receptor of the secretion signal with a polypeptide coded by the insert DNA.

An upstream translatable DNA sequence encodes a prokaryotic secretion signal as described earlier. The upstream translatable DNA sequence encoding the pelB secretion signal is a preferred DNA sequence for inclusion in a receptor expression vector. A downstream translatable DNA sequence encodes a filamentous phage membrane anchor as described earlier. Thus, a downstream translatable DNA sequence encodes an amino acid residue sequence that corresponds, and preferably is identical, to the membrane anchor domain of either a filamentous phage gene III or gene VIII coat polypeptide.

A cassette in a DNA expression vector of this invention is the region of the vector that forms, upon insertion of a translatable DNA sequence (insert DNA), a sequence of nucleotides capable of expressing, in an appropriate host, a receptor polypeptide. The expression-competent sequence of nucleotides is referred to as a cistron. Thus, the cassette comprises DNA expression control elements operatively linked to the upstream and downstream translatable DNA sequences. A cistron is formed when a translatable DNA sequence is directionally inserted (directionally ligated) between the upstream and downstream sequences via the sequence of nucleotides adapted for that purpose. The resulting three translatable DNA sequences, namely the upstream, the inserted and the downstream sequences, are all operatively linked in the same reading frame.

Thus, a DNA expression vector for expressing heterodimeric receptors provides a system for cloning translatable DNA sequences into the cassette portions of the vector to produce cistrons capable of expressing the first and second receptor polypeptides of a heterodimeric receptor, such as the heavy and light chain of a monoclonal antibody. An expression vector, whether it is used to express the heterologous fusion polypeptide or a heterodimeric receptor, is characterized as being capable of expressing, in a compatible host, a structural gene product.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier.

As used herein with regard to DNA sequences or segments, the phrase "operatively linked" means the sequences or segments have been covalently joined, preferably by conventional phosphodiester bonds, into one strand of DNA, whether in single or double stranded form. The choice of vector to which transcription unit or a cassette of this invention is operatively linked depends directly, as is well known in the art, on the functional properties desired, e.g., vector replication and protein expression, and the host cell to be transformed, these being limitations inherent in the art of constructing recombinant DNA molecules.

A sequence of nucleotides adapted for directional ligation, i.e., a polylinker, is a region of the DNA expression vector that (1) operatively links for replication and transport the upstream and downstream translatable DNA sequences and (2) provides a site or means for directional ligation of a DNA sequence into the vector. Typically, a directional polylinker is a sequence of nucleotides that defines two or more restriction endonuclease recognition sequences, or restriction sites. Upon restriction cleavage, the two sites yield cohesive termini to which a translatable DNA sequence can be ligated to the DNA expression vector. Preferably, the two restriction sites provide, upon restriction cleavage, cohesive termini that are non-complementary and thereby permit directional insertion of a translatable DNA sequence into the cassette. In one embodiment, the directional ligation means is provided by nucleotides present in the upstream translatable DNA sequence, downstream translatable DNA sequence, or both. In another embodiment, the sequence of nucleotides adapted for directional ligation comprises a sequence of nucleotides that defines multiple directional cloning means. Where the sequence of nucleotides adapted for directional ligation defines numerous restriction sites, it is referred to as a multiple cloning site.

In a preferred embodiment, a DNA expression vector is designed for convenient manipulation in the form of a filamentous phage particle encapsulating a genome according to the teachings of the present invention. In this embodiment, a DNA expression vector further contains a nucleotide sequence that defines a filamentous phage origin of replication such that the vector, upon presentation of the appropriate genetic complementation, can replicate as a filamentous phage in single stranded replicative form and be packaged into filamentous phage particles. This feature provides the ability of the DNA expression vector to be packaged into phage particles for subsequent segregation of the particle, and vector contained therein, away from other particles that comprise a population of phage particles.

A filamentous phage origin of replication is a region of the phage genome, as is well known, that defines sites for initiation of replication, termination of replication and packaging of the replicative form produced by replication (see, for example, Rasched, et al., *Microbiol. Rev.*, 50:401-427, 1986; and Horiuchi, *J. Mol. Biol.*, 188:215-223, 1986).

A preferred filamentous phage origin of replication for use in the present invention is an M13, f1 or fd phage origin of replication (Short, et al. (*Nucl. Acids Res.*, 16:7583-7600, 1988). Preferred DNA expression vectors are the dicistronic expression vectors pCOMB8, pCKAB8, pCOMB2-8, pCOMB3, pCKAB3, pCOMB2-3 and pCOMB2-3'.

The invention now being fully described, it will be apparent to one of ordinary skill in the art that various changes and modifications can be made without departing from the spirit or scope of the invention.

EXAMPLE 1

Construction of a Dicistronic Expression Vector for Producing a Heterodimeric Receptor on Phage Particles To obtain a vector system for generating a large number of Fab antibody fragments that can be screened directly, expression libraries in bacteriophage Lambda have previously been constructed as described in Huse, et al. (*Science*, 246:1275-1281, 1989). However, these systems did not contain design features that provide for the expressed Fab to be targeted to the surface of a filamentous phage particle as described by Barbas, et al. (*Proc. Natl. Acad. Sci. USA*, 33:7978-7982, 1991).

The main criterion used in choosing a vector system was the necessity of generating the largest number of Fab fragments which could be screened directly. Bacteriophage Lambda was selected as the starting point to develop an expression vector for three reasons. First, in vitro packaging of phage DNA was the most efficient method of reintroducing DNA into host cells. Second, it was possible to detect protein expression at the level of single phage plaques. Finally, the screening of phage libraries typically involved less difficulty with nonspecific binding. The alternative, plasmid cloning vectors, are only advantageous in the analysis of clones after they have been identified. This advantage was not lost in the present system because of the use of a dicistronic expression vector such as pCombVIII, thereby permitting a plasmid containing the heavy chain, light chain, or Fab expressing inserts to be excised.

a. Construction of Dicistronic Expression Vector pCOMB (i) Preparation of Lambda Zap™ II Lambda Zap™ II is a derivative of the original Lambda Zap (ATCC #40,298) that maintains all of the characteristics of the original Lambda Zap including 6 unique cloning sites, fusion protein expression, and the ability to rapidly excise the insert in the form of a phagemid (Bluescript SK–), but lacks the SAM 100 mutation, allowing growth on many Non-Sup F strains, including XL1-Blue. The Lambda Zap™ II was constructed as described in Short, et al. (*Nuc. Acids Res.*, 16:7583-7600, 1988), by replacing the lambda S gene contained in a 4254 base pair (bp) DNA fragment produced by digesting lambda Zap with the restriction enzyme Nco I. This 4254 bp DNA fragment was replaced with the 4254 bp DNA fragment containing the Lambda S gene isolated from Lambda gt10 (ATCC #40,179) after digesting the vector with the restriction enzyme Nco I. The 4254 bp DNA fragment isolated from lambda gt10 was ligated into the original lambda Zap vector using T4 DNA ligase and standard protocols such as those described in *Current Protocols in Molecular Biology*, Ausubel, et al., eds., John Wiley and Sons, New York, 1987, to form Lambda ZaP™ II.

(ii) Preparation of Lambda Hc2

To express a plurality of $V_H$-coding DNA homologs in an *E. coli* host cell, a vector designated Lambda Hc2 was constructed. The vector provided the following: the capacity to place the $V_H$-coding DNA homologs in the proper reading frame; a ribosome binding site as described by Shine, et al. (*Nature*, 254:34, 1975); a leader sequence directing the expressed protein to the periplasmic space designated the pelB secretion signal; a polynucleotide sequence that coded for a known epitope (epitope tag); and also a polynucleotide that coded for a spacer protein between the $V_H$-coding DNA homolog and the polynucleotide coding for the epitope tag. Lambda Hc2 has been previously described by Huse, et al. (*Science*, 246:1274-1281, 1989).

To prepare Lambda Hc2, a synthetic DNA sequence containing all of the above features was constructed by designing single stranded polynucleotide segments of 20-40 bases that would hybridize to each other and form the double stranded synthetic DNA sequence. The individual single-stranded polynucleotide segments are shown in Table 1.

Polynucleotides N2, N3, N9-4, N11, N10-5, N6, N7 and N8 (Table 1) were kinased by adding 1 μl of each polynucleotide (0.1 μg/μl) and 20 units of $T_4$ polynucleotide kinase to a solution containing 70 mM Tris-HCl, pH 7.6, 10 mM $MgCl_2$, 5 mM dithiothreitol (DTT), 10 mM beta-mercaptoethanol, 500 micrograms per milliliter (μg/ml) bovine serum albumin (BSA). The solution was maintained at 37 degrees Centigrade (37° C.) for 30 minutes and the reaction stopped by maintaining the solution at 65° C. for 10 minutes. The two end polynucleotides, 20 mg of polynucleotides N1 and polynucleotides N12, were added to the above kinasing reaction solution together with ¹/₁₀ volume of a solution containing 20.0 mM Tris-HCl, pH 7.4, 2.0 mM $MgCl_2$ and 50.0 mM NaCl. This solution was heated to 70° C. for 5 minutes and allowed to cool to room temperature, approximately 25° C., over 1.5 hours in a 500 ml beaker of water. During this time period all 10 polynucleotides annealed to form a double stranded synthetic DNA insert. The individual polynucleotides were covalently linked to each other to stabilize the synthetic DNA insert by adding 40 μl of the above reaction to a solution containing 50 mM Tris-HCl, pH 7.5, 7 mM $MgCl_2$, 1 mM DTT. 1 mM adenosine triphosphate (ATP) and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 μl of the above reaction, 4 μl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

TABLE 1

| | |
|---|---|
| N1) | 5' GGCCGCAAATTCTATTTCAAGGAGAC (SEQ ID 3) AGTCAT 3' |
| N2) | 5' AATGAAATACCTATTGCCTACGGCAG (SEQ. I.D. 4) CCGCTGGATT 3' |
| N3) | 5' GTTATTACTCGCTGCCCAACCAGCCA (SEQ. I.D. 5) TGGCCC 3' |
| N6) | 5' CAGTTTCACCTGGGCCATGGCTGGTT (SEQ. I.D. 6) GGG 3' |
| N7) | 5' CAGCGAGTAATAACAATCCAGCGGCT (SEQ. I.D. 7) GCCGTAGGCAATAG3' |
| N8) | 5' GTATTTCATTATGACTGTCTCCTTGA (SEQ. I.D. 8) AATAGAATTTGC 3' |
| N9-4) | 5' AGGTGAAACTGCTCGAGATTTCTAGA (SEQ. I.D. 9) CTAGTTACCCGTAC 3' |
| N10-5) | 5' CGGAACGTCGTACGGGTAACTAGTCT (SEQ. I.D. 10) AGAAATCTCGAG 3' |
| N11) | 5' GACGTTCCGGACTACGGTTCTTAATA (SEQ. I.D. 11) GAATTCG 3' |

TABLE 1-continued

N12) 5' TCGACGAATTCTATTAAGAACCGTAG (SEQ. I.D. 12)
    TC 3'

The completed synthetic DNA insert was ligated directly into the Lambda Zap™ II vector described in Example 1a(i) that had been previously digested with the restriction enzymes, Not I and Xho I. The ligation mixture was packaged according to the manufacture's instructions using Gigapack II Gold packing extract available from Stratagene, La Jolla, Calif. The packaged ligation mixture was plated on XL1-Blue cells (Stratagene). Individual Lambda plaques were cored and the inserts excised according to the in vivo excision protocol for Lambda Zap™ II provided by the manufacturer (Stratagene). This in vivo excision protocol moved the cloned insert from the Lambda Hc2 vector into a phagemid vector to allow for easy manipulation and sequencing. The accuracy of the above cloning steps was confirmed by sequencing the insert using the Sanger dideoxy method described in by Sanger, et al. (*Proc. Natl. Acad. Sci. USA*, 74:5463-5467, 1977), and using the manufacture's instructions in the AMV Reverse Transcriptase $^{35}$S-ATP sequencing kit (Stratagene). The resultant Lambda Hc2 expression vector is shown in FIG. 1.

(iii) Preparation of Lambda Lc2

To express a plurality of $V_L$-coding DNA homologs in an *E. coli* host cell, a vector designated Lambda Lc2 was constructed having the capacity to place the $V_L$-coding DNA homologs in the proper reading frame, provided a ribosome binding site as described by Shine, et al. (*Nature*, 254:34, 1975), provided the pelB gene leader sequence secretion signal that has been previously used to successfully secrete Fab fragments in *E. coli* by Lei, et al. (*J. Bac.*, 169:4379, 1987) and Better, et al. (*Science*, 240:1041, 1988), and also provided a polynucleotide containing a restriction endonuclease site for cloning. Lambda Lc2 has been previously described by Huse, et al. (*Science*, 246:1275-1281, 1989).

A synthetic DNA sequence containing all of the above features was constructed by designing single stranded polynucleotide segments of 20-60 bases that would hybridize to each other and form the double stranded synthetic DNA. The sequence of each individual single-stranded polynucleotide segment (01-08) within the double stranded synthetic DNA sequence is shown in Table 2.

Polynucleotides shown in Table 2 were kinased by adding 1 µl (0.1 µg/µl) of each polynucleotide and 20 units of $T_4$ polynucleotide kinase to a solution containing 70 mM Tris-HCl, pH 7.6, 10 mM MgCl, 5 mM DTT, 10 mM betamercaptoethanol, 500 mg/ml of BSA. The solution was maintained at 37° C. for 30 minutes and the reaction stopped by maintaining the solution at 65° C. for 10 minutes. The 20 ng each of the two end polynucleotides, 01 and 08, were added to the above kinasing reaction solution together with ¹⁄₁₀ volume of a solution containing 20.0 mM Tris-HCl, pH 7.4, 2.0 mM MgCl and 15.0 mM sodium chloride (NaCl). This solution was heated to 70° C. for 5 minutes and allowed to cool to room temperature, approximately 25° C., over 1.5 hours in a 500 ml beaker of water. During this time period all 8 polynucleotides annealed to form the double stranded synthetic DNA insert shown in FIG. 3. The individual polynucleotides were covalently linked to each other to stabilize the synthetic DNA insert by adding 40 µl of the above reaction to a solution containing 50 ml Tris-HCl, pH 7.5, 7 ml MgCl, 1 mm DTT, 1 mm ATP and 10 units of T4 DNA ligase. This solution was maintained at 37° C. for 30 minutes and then the T4 DNA ligase was inactivated by maintaining the solution at 65° C. for 10 minutes. The end polynucleotides were kinased by mixing 52 A1 of the above reaction, 4 µl of a solution containing 10 mM ATP and 5 units of T4 polynucleotide kinase. This solution was maintained at 37° C. for 30 minutes and then the T4 polynucleotide kinase was inactivated by maintaining the solution at 65° C. for 10 minutes.

TABLE 2

| 1. | 5' TGAATTCTAAACTAGTCGCCAAGGAGAC AGTCAT 3' | (SEQ. I.D. 13) |
| 2. | 5' AATGAAATACCTATTGCCTACGGCAGCC GCTGGATT 3' | (SEQ. I.D. 14) |
| 3. | 5' GTTATTACTCGCTGCCCAACCAGCCATG GCC 3' | (SEQ. I.D. 15) |
| 4. | 5' GAGCTCGTCAGTTCTAGAGTTAAGCGGC CG 3' | (SEQ. I.D. 16) |
| 5. | 5' CTATTTCATTATGACTGTCTCCTTGGCG ACTAGTTTAGAATTCAAGCT 3' | (SEQ. I.D. 17) |
| 6. | 5' CAGCGAGTAATAACAATCCAGCGGCTGC CGTAGGCAATAG 3' | (SEQ. I.D. 18) |
| 7. | 5' TGACGAGCTCGGCCATGGCTGGTTGG G 3' | (SEQ. I.D. 19) |
| 8. | 5' TCGACGGCCGCTTAACTCTAGAAC 3' | (SEQ. I.D. 20) |

Figure 2:
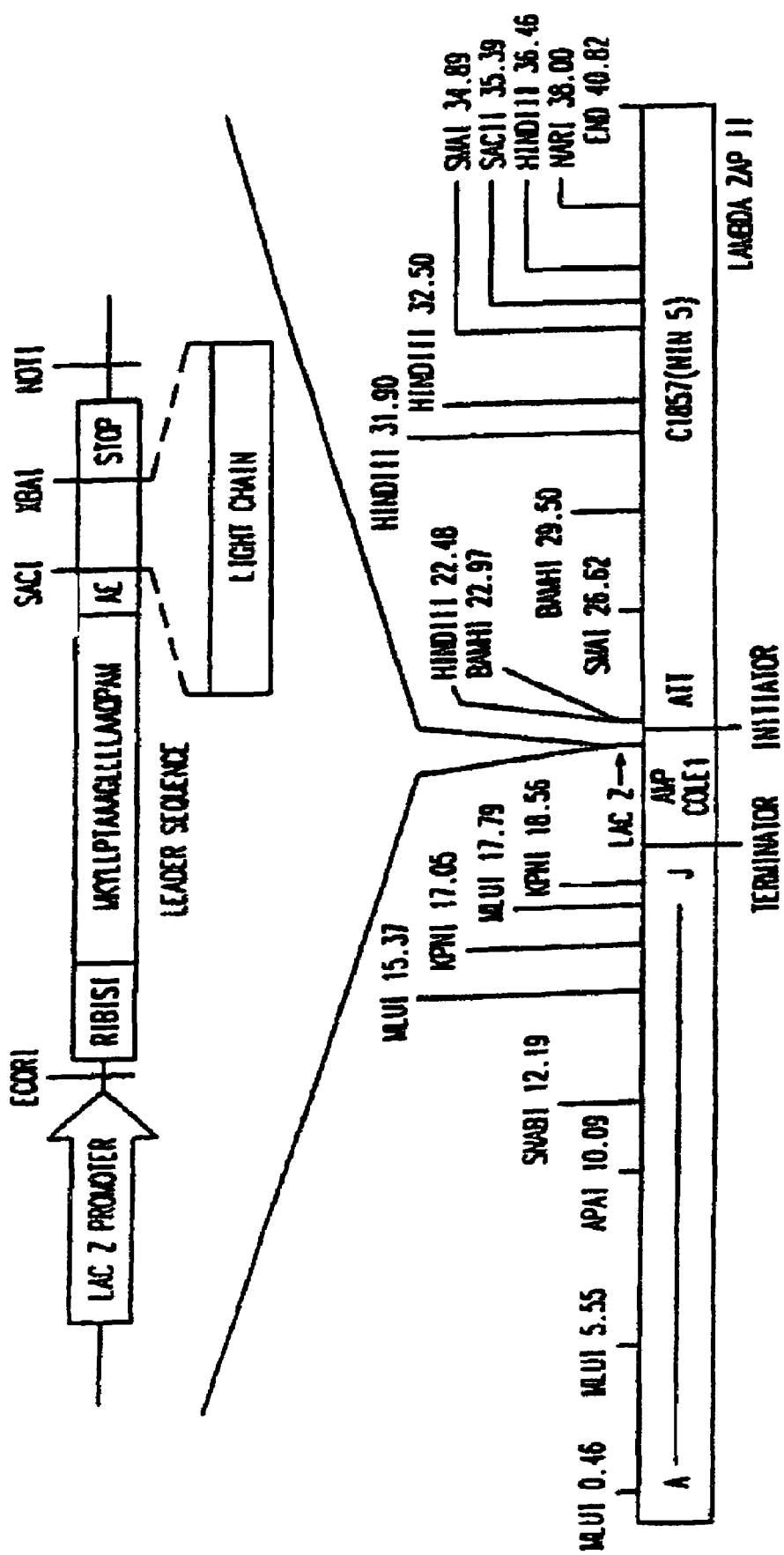
FIG. 2 shows the Lc2 expression vector, (SEQ ID NO:35)

The completed synthetic DNA insert was ligated directly into the Lambda Zap™ II vector described in Example 1(a)(i) that had been previously digested with the restriction enzymes Sac I and Xho I. The ligation mixture was packaged according to the manufacture's instructions using Gigapack II Gold packing extract (Stratagene). The packaged ligation mixture was plated on XL1-Blue cells (Stratagene). Individual Lambda plaques were cored and the inserts excised according to the in vivo excision protocol for lambda Zap™ II provided by the manufacturer (Stratagene). This in vivo excision protocol moved the cloned insert from the Lambda Lc2 vector into a plasmid phagemid vector allow for easy manipulation and sequencing. The accuracy of the above cloning steps was confirmed by sequencing the insert using the manufactures instructions in the AMV Reverse Transcriptase $^{35}$S-dATP-sequencing kit (Stratagene). The resultant Lc2 vector is schematically diagramed in FIG. 2.

A preferred vector for use in this invention, designated Lambda Lc3, is a derivative of Lambda Lc2 prepared above. Lambda Lc2 contains a Spe I restriction site (ACTAGT) located 3' to the EcoR I restriction site and 5' to the Shine-Dalgarno ribosome binding site. A Spe I restriction site is also present in Lambda Hc2 as shown in FIG. 1. A combinatorial vector, designated pComb, was constructed by combining portions of Lambda Hc2 and Lc2 together as described in Example 1a(iv) below. The resultant combinatorial pComb vector contained two Spe I restriction sites, one provided by Lambda Hc2 and one provided by Lambda Lc2, with an EcoR I site in between. Despite the presence of two Spe I restriction sites, DNA homologs having Spe I and EcoR I cohesive termini were successfully directionally ligated into a pComb expression vector previously digested with Spe I and EcoR I. The proximity of the EcoR I restriction site to the 3' Spe I site, provided by the Lc2 vector, inhibited the complete digestion of the 3' Spe I site.

Thus, digesting pComb with Spe I and EcoR I did not result in removal of the EcoR I site between the two Spe I sites.

The presence of a second Spe I restriction site may be undesirable for ligations into a pComb vector digested only with Spe I as the region between the two sites would be eliminated. Therefore, a derivative of Lambda Lc2 lacking the second or 3' Spe I site, designated Lambda Lc3, is produced by first digesting Lambda Lc2 with Spe I to form a linearized vector. The ends are filled in to form blunt ends which are ligated together to result in Lambda Lc3 lacking a Spe I site. Lambda Lc3 is a preferred vector for use in constructing a combinatorial vector as described below.

(iv) Preparation of pComb

Phagemids were excised from the expression vectors lambda Hc2 or Lambda Lc2 using an in vivo excision protocol described above. Double stranded DNA was prepared from the phagemid-containing cells according to the methods described by Holmes, et al. (*Anal. Biochem.*, 114: 193, 1981). The phagemids resulting from in vivo excision contained the same nucleotide sequences for antibody fragment cloning and expression as did the parent vectors, and are designated phagemid Hc2 and Lc2, corresponding to Lambda Hc2 and Lc2, respectively.

Figure 3:
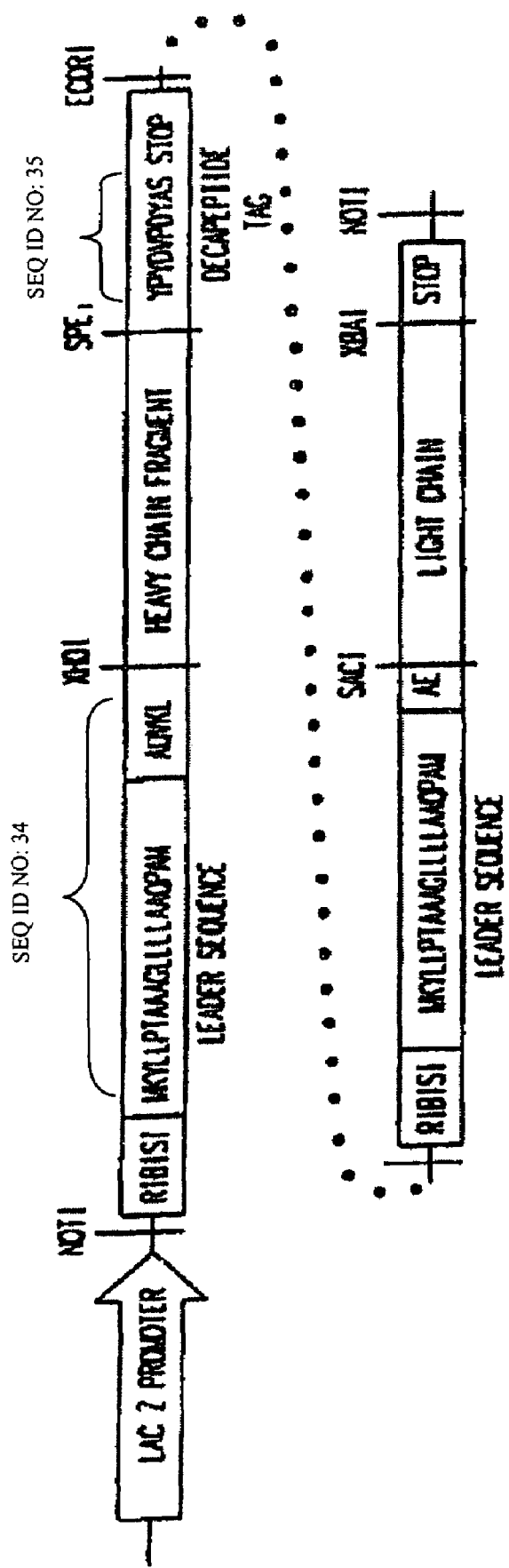
FIG. 3 shows the schematic organization of the pComb combinatorial phagemid vector, (SEQ ID Nos:34 (top) and 35 (bottom)).

For the construction of combinatorial phagemid vector pComb, produced by combining portions of phagemid Hc2 and phagemid Lc2, phagemid Hc2 was first digested with Sac I to remove the restriction site located 5' to the LacZ promoter. The linearized phagemid was then blunt ended with T4 polymerase and ligated to result in a Hc2 phagemid lacking a Sac I site. The modified Hc2 phagemid and the Lc2 phagemid were then separately restriction digested with Sca I and EcoR I to result in a Hc2 fragment having from 5' to 3' Sca I, not I Xho I, Spe I and EcoR I restriction sites and a Lc2 fragment having from 5' to 3' EcoR 1, Sac I, Xba I and Sac I restriction sites. The linearized phagemids were then ligated together at their respective cohesive ends to form pComb, a circularized phagemid having a linear arrangement of restriction sites of Not I, Xho I, Spe I, EcoR I, Sac I, Xba I, Apa I and Sca I. The ligated phagemid vector was then inserted into an appropriate bacterial host and transformants were selected on the antibiotic ampicillin. Selected ampicillin resistant transformants were screened for the presence of two Not I sites. The resulting ampicillin resistant combinatorial phagemid vector was designated pComb, the schematic organization of which is shown in FIG. 3. The resultant combinatorial vector, pComb, consisted of a DNA molecule having two cassettes to express two fusion proteins and having nucleotide residue sequences for the following operatively linked elements listed in a 5' to 3' direction: a first cassette consisting of an inducible LacZ promoter upstream from the LacZ gene; a Not I restriction site; a ribosome binding site; a pelB leader; a spacer; a cloning region bordered by a 5' Xho and 3' Spe I restriction site; a decapeptide tag followed by expression control stop sequences; an EcoR I restriction site located 5' to a second cassette consisting of an expression control ribosome binding site; a pelB leader; a spacer region; a cloning region bordered by a 5' Sac I and a 3' Xba I restriction site followed by expression control stop sequences and a second Not I restriction site.

A preferred combinatorial vector designated pComb3, is constructed by combining portions of phagemid Hc2 and phagemid Lc3 as described above for preparing pComb. The resultant combinatorial vector, pComb3, consists of a DNA molecule having two cassettes identical to pComb to express two fusion proteins identically to pComb except that a second Spe I restriction site in the second cassette is eliminated.

b. Construction of Vectors pCombVIII and pCombIII for Expressing Fusion Proteins Having a Bacterlophage Coat Protein Membrane Anchor Because of the multiple endonuclease restriction cloning sites, the pComb phagemid expression vector prepared above is a useful cloning vehicle for modification for the preparation of an expression vector of this invention. To that end, pComb is digested with EcoR I and Spe I followed by phosphatase treatment to produce linearized pComb.

(i) Preparation of pCombVIII

A PCR product having a nucleotide sequence that defines a filamentous bacteriophage coat protein VIII (cpVIII) membrane anchor domain and cohesive Spe I and EcoR I termini was admixed with the linearized pComb to form a ligation admixture. The cpVIII-membrane anchor-encoding PCR fragment was directionally ligated into the pComb phagemid expression vector at corresponding cohesive termini, that resulted in forming pComb VIII (also designated pComb8). pCombVIII contains a pelB secretion signal operatively linked to the cpVIII membrane anchor.

A preferred phagemid expression vector for use in this invention, designated either pComb2-VIII or pComb2-8, was prepared as described above by directionally ligating the cpVIII membrane anchor-encoding PCR fragment into a pComb2 phagemid expression vector via Spe I and EcoR I cohesive termini. The pComb2-8 had only one Spe I restriction site.

(ii) Preparation of pCombIII

A separate phagemid expression vector was constructed using sequences encoding bacteriophage cpIII membrane anchor domain. A PCR product defining the cpIII membrane anchor containing a LacZ promotor region sequence 3' to the membrane anchor for expression of the light chain and Spe I and EcoR I cohesive termini was prepared. The cpIII-derived PCR product was then ligated into linearized pComb2 vector having only one Spe I site to form the vector pComb2-3 (also designated pComb2-III).

A more preferred phagemid expression vector for use in this invention having additional restriction enzyme cloning sites, designated pComb-III' or PComb2-3', was prepared as described above for pComb2-3 with the addition of a 51 base pair fragment from pBluescript as described by Short, et al. (*Nuc. Acids Res.*, 16:7583-7600, 1988) and commercially available from Stratagene. To prepare pComb2-3', pComb2-3 was first digested with Xho I and Spe I restriction enzymes to form a linearized pComb2-3. The vector pBluescript was digested with the same enzymes releasing a 51 base pair fragment containing the restriction enzyme sites SI I, Acc I, Hinc II, Cla I, Hind III, EcoR V, Pst I, Sma I and BamH I. The 51 base pair fragment was ligated into the linearized pComb2-3 vector via the cohesive Xho I and Spe I termini to form pComb2-3.

EXAMPLE 2

Isolation of RSV-Specific Monoclonal Antibodies

Lymphocyte RNA preparation and library construction. The preparation of RNA from the bone marrow lymphocytes of an HIV-1 seropositive individual and construction of an IgG1x Fab library on the surface of phage using the pComb3 system were achieved as described previously (Burton, et al., *Proc. Natl. Acad. Sci.* USA 88:10134, 1991).

Panning of the library to select antigen binding phage, preparation of soluble Fabs and ELISA screening of Fab supernatants. ELISA analysis of the serum of the HIV-1 seropositive donor described in Burton, et al., supra, indicated a titer of approximately 1:3000 to RSV FG glycoprotein, therefore the same library was panned against recombinant FG glycoprotein coated on ELISA wells (1 μg/well of baculovirus-expressed FG fusion glycoprotein). Panning of the library was carried out as described (Barbas, et al., *Proc. Natl. Acad. Sci. USA*, 33:7978, 1991). Four rounds of panning produced an amplification in eluted phage of a factor of about 500, indicating enrichment for specific antigen-binding clones. Eluted phage were used to infect *E. coli* XL1-Blue cells. Soluble Fabs were generated by DNA preparation from the cells and Nhel, Spel excision of the phage coat protein gene III fragment followed by religation. The reconstructed phagemid were used to transform XL1-Blue cells to produce clones secreting soluble Fab fragments. Fab supernates were prepared by sonication of pelleted cells as described by Burton, supra. Briefly, clones were grown in 10 ml SB (super broth; 30 g tryptone, 20 g yeast extract, 10 g MOPS per liter, pH 7) containing 50 μg/ml carbenicillin and 10 mM $MgCl_2$ at 37° C. until an $OD_{600}$ of 0.2 was achieved. Isopropyl-(beta)-D-thiogalactopyranoside, (IPTG), 1 mM, was added and the culture grown overnight at 37° C. Cells were pelleted by centrifugation at 4000 rpm for 15 minutes in a Beckman JA10 rotor at 4° C. Cells were resuspended in 3 ml of PBS containing 0.2 mM phenylmethylsulfonyl fluoride and lysed by sonication on ice (2-4 minutes). The debris was pelleted by centrifugation at 14,000 rpm in a JA-20 rotor at 4° C. for minutes. The supernatant was used directly for ELISA analysis. As an alternative to sonication, Fab supernates were prepared by a freeze-thaw lysis protocol. Growth conditions were as described above for sonication, but after IPTG was added, cells were grown at 25° C. to 39° C. overnight. Cells were resuspended in 1 ml PBS in a microfuge tube, frozen on dry ice and then thawed in a 37° C. water bath. The freeze-thawing procedure was repeated 3 times and the supernatant collected after spinning in a microfuge for 10 minutes. The supernatant was used directly for ELISA analysis and was stored at −20° C.

ELISA screening of Fab supernatants was as described (Barbas, et al., *Methods: A Comparison to Methods in Enzymol.*, Lerner, R. and Burton, D. eds., 2:119, 1991). ELISA wells were coated with 0.1 μg of either FG-fusion glycoprotein or purified F glycoprotein. Thirty clones were grown up and the supernates containing Fab fragments screened in an ELISA assay for reactivity with FG. The supernates from 28 clones showed clear reactivity. All of these positive clones also reacted with F glycoprotein.

Virus neutralization assay. Neutralizing activity was measured by complement-enhanced plaque reduction (Coates, et al., *J. Epid.*, 83:299, 1966) using HEp-2 cell cultures and prototype subgroup A (strain A2) and subgroup B (strain 18537) viruses as well as subgroup A and β isolates of diverse origin. Titer of neutralizing antibody was calculated as the highest dilution of Fab that reduced plaque number by 60%.

The 28 positive supernates were screened for their ability to neutralize subgroup A RSV in a plaque assay. Fab supernates of clones 13 and 19 neutralized this virus with high efficiency and a high concentration of Fab neutralized virus completely (Table 3). Three separate supernate preparations of each clone neutralized RSV in a reproducible manner with an efficiency of 0.9 to 2.8 nM, i.e. 0.04 to 0.14 μg/ml of Fab reduced RSV plaque titer by 60%. The other supernates showed some weak ability to neutralize virus but this was somewhat variable. The most consistent neutralization from among these clones was observed with clone 11. This clone did not neutralize RSV completely and its efficiency of neutralization was approximately 10-fold less than clones 13 and 19 (Table 3).

Purification of Fabs. One liter cultures of super broth containing 50 μg/ml carbenicillin and 20 mM $MgCl_2$ were inoculated with appropriate clones and induced 7 hours later with 2 mM IPTG and grown overnight at 30° C. The cell pellets were sonicated and the supernatant concentrated to 50 ml. The filtered supernatants were loaded on a 25 ml protein G-anti-Fab column, washed with 12 ml buffer at 3 ml/min., and eluted with citric acid, pH 2.3. The neutralized fractions were then concentrated and exchanged into 50 mM MES pH 6.0 and loaded onto a 2 ml Mono-S column at 1 ml/min. A gradient of 0-500 mM NaCl was run at 1 ml/min with the Fab eluting in the range of 200-250 mM NaCl. After concentration, the Fabs were positive when titered by ELISA against FG and gave a single band at 50 kD by 10-15% SDS-PAGE. Concentration was determined by absorbance measurement at 280 nm using an extinction coefficient (1 mg/ml) of 1.35. Fabs of clones 11, 13 or 19 purified and concentrated from *E. coli* lysates by affinity chromatography also neutralized RSV with relatively high efficiency similar to but somewhat less than that observed for crude lysates. Specificity of the neutralizing activity exhibited by clones 11 and 19 was provided by the finding that purified concentrated Fabs did not neutralize parainfluenza type 3 virus (Table 3). Furthermore, a purified concentration Fab preparation with specificity for HIV-gp1 gp120 (ELISA titer of 1:1500) did not neutralize RSV (Table 3).

TABLE 3

NEUTRALIZING ACTIVITY AND SPECIFICITY OF THREE HUMAN MONOCLONAL Fabs DIRECTED AGAINST RSV (SUBGROUP A) F GLYCOPROTEIN

| Specificity for | Fab Clone Designation | Material Tested | Highest Fab Concentration Tested (μg/ml) | Maximum Neutralization of RSV (Subgroup A) | Concentration of Fab Needed for 60% Plaque Reduction (μg/ml) | |
|---|---|---|---|---|---|---|
| | | | | | RSV | Parainfluenza Type 3 Virus |
| RSV F | 13* | *E. coli* lysates | 6.75; 1.8; 1.24 | 100% | 0.1; 0.06; 0.14 | NT** |
| | | Purified from Lysate | 1.16 | 98% | 0.2 | >2.3 |

TABLE 3-continued

NEUTRALIZING ACTIVITY AND SPECIFICITY OF THREE HUMAN MONOCLONAL Fabs DIRECTED AGAINST RSV (SUBGROUP A) F GLYCOPROTEIN

| Fab Clone | | | Highest Fab | Maximum | Concentration of Fab Needed for 60% Plaque Reduction (µg/ml) | |
|---|---|---|---|---|---|---|
| Specificity for | Designation | Material Tested | Concentration Tested (µg/ml) | Neutralization of RSV (Subgroup A) | RSV | Parainfluenza Type 3 Virus |
| | 19* | E. coli Lysates | 0.75; 0.75; 1.4 | 93-100% | 0.07; 0.04; 0.08 | NT |
| | | Purified from lysate | 84.25 | 100% | 0.4 | >169 |
| | 11 | E. coli lysate | 2.4 | 59% | >2.4; 1.6 | NT |
| | | Purified from lysate | 85 | 88% | 1.8 | >170 |
| HIV-1 | HIV | Purified from lysate | 18.6 | 0 | >37 | >37 |

*Identical Fab sequence
**Not Tested

EXAMPLE 3

Neutralizing Activity of Fab Against Diverse RSV Isolates

The breadth of neutralizing activity of clone 19 was examined by testing it against an additional 9 subgroup A virus isolates as well as 9 subgroup B virus isolates. These viruses were recovered in different geographic areas over a period of 31 years. Virus neutralization was performed as described in Example 2. The purified Fab 19 preparation neutralized each of these preparations with high efficiency (Table 4). Additional studies showed that clone 11 also appears to have broad reactivity because it neutralized the subgroup B RSV prototype as efficiently as the subgroup A prototype and had broad neutralizing activity against the subgroup A and B viruses.

TABLE 4

NEUTRALIZING ACTIVITY OF Fab CLONE 19 AGAINST DIVERSE RSV ISOLATES BELONGING TO ANTIGENIC SUBGROUP A OR B

| RSV Isolates Tested | | | Specific Neutralizing Activity of Fab Clone 19 |
|---|---|---|---|
| Antigenic Subgroup | No. Isolates | Temporal Distribution | (Conc. of Fab (µg/ml) Needed for 60% Plaque Reduction) |
| A | 10 | 1959-1984 | 0.3; 0.3; 0.4; 0.7; 1.0; 1.1; 1.2; 1.2; 1.7; 3.0* |
| B | 9 | 1962-1990 | <0.2; 0.3; 0.4; 0.4; 0.4; 0.4; 0.5; 0.6; 0.8** |

*Washington/Bern/65, St. Louis/10865/84, Australia/AZ/61, St. Louis/863/84, Washington/343/67, Australia/A1/61, Washington/11657/60, St. Louis/10849/84, Washington/3199/66, Sweden/669/59, respectively.
**West Virginia (WV)/14617/85, WV/17154/85, WV/4843/81, WV20323/87, WV/401R/90, Washington/18537/62, WV/474/R90, WV/285R/90, WV1293/79, respectively. (West Virginia strains kindly provided by Maurice A. Mufson, M.D.).

EXAMPLE 4

Nucleic Acid Sequence Analysis Comparison Between RSV-Specific Monoclonal Antibody Clones Nucleic acid sequencing was carried out on double stranded DNA using Sequenase 1.0 (USB) and the appropriate primers hybridizing to sequences in the Cγ1 domain (SEQGb:5'-GTCGTTGACCAGGCAGCCCAG-3') SEQ ID No:30 or the Cχ domain (SEQKb:5'-ATAGAAGTTGT-TCAGCAGGCA-3') SEQ ID No:31. Alternatively sequencing employed single stranded DNA and the T3 primer (5'-ATTAACCCTCACTAAAG-3'SEQ ID No:32, Sambrook, et al., Molecular Cloning: A Laboratory Manual, 2nd edn. Cold Spring Harbor Press, New York, 1989) or one hybridizing to a sequence in the Cχ domain (KEF:5'-GAATTCTAAACTAGCTAGTTCG-3'SEQ ID No:33).

Figure 5A:
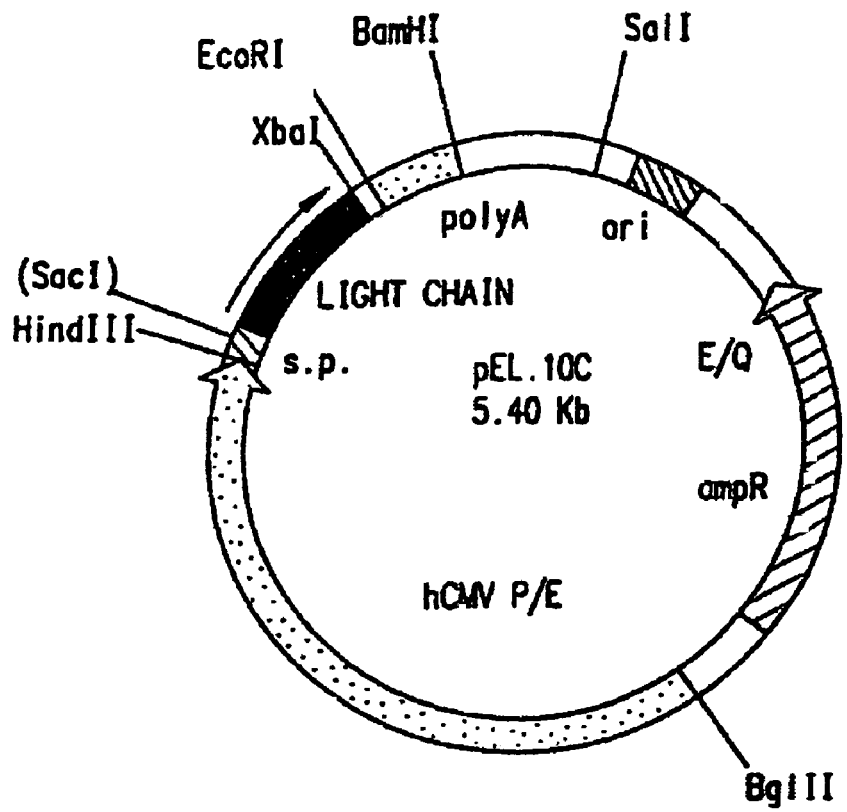
FIG. 5a shows the vector used for the expression of the kappa light chains fused to a signal peptide (s.p.) under transcriptional control of the hCMV promoter-enhancer element (hCMV P/E), polyadenylation is provided by the SV 40 early polyadenylation signal sequence (poly A). The plasmid has a ColE1 origin of replication (ori) and an ampicillin resistance gene (ampR) for selection in E. coli. The DNA liker sequence encoding the signal peptide and the first 3 N-terminal aa (in 1 letter code) of the mature protein are shown underneath (nucleic and amino acid sequences are SEQ ID Nos:26 and 27; the complementary strand is SEQ ID NO:36). The arrow indicates the signal peptide cleavage site. The third aa is either Q or E, depending on the linker used. The SacI site is in brackets, because it is destroyed in pEL 10 CQ.
Figure 5B:
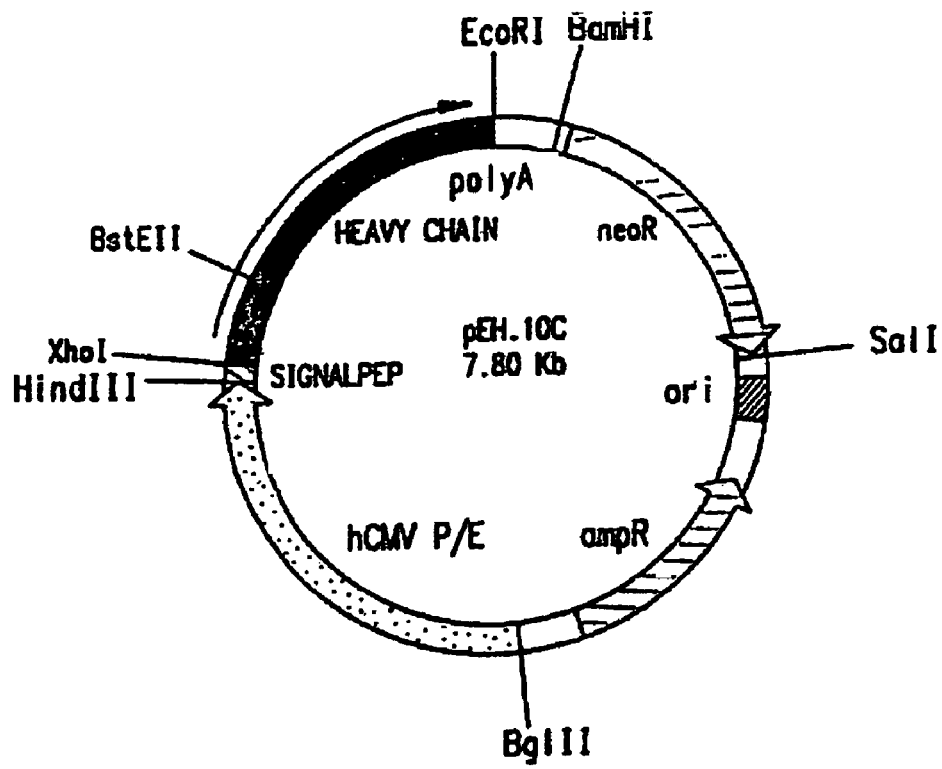
FIG. 5b shows pEH. 10C, the vector used for the expression of the IgG1 heavy chain. The BstEII site in domain Cgamma1, which has been used for the fusion of the cloned Fd to the constant part is indicated. In addition to the features of the light chain construct, this vector has a neomycin resistance (NeoR) gene for selection in eukaryotes. The DNA sequence encoding the signal peptide is shown underneath (SEQ ID Nos:28 and 29, respectively). The complementary strand is also shown (SEQ ID NO:37).

To reveal any relationship between clones, clones 13 and 19 (clones that neutralized efficiently), clone 11, and 4 other clones (chosen randomly) were sequenced. As shown in FIG. 5, clones 13 and 19 were identical in both heavy and light chain variable domains and were clearly distinct from the other 5 clones. Nonetheless, clone 19 and clone 11 did not exhibit any evidence of synergy when these two Fabs were tested as a mixture adjusted to create an equal neutralizing activity for each component. The heavy chains of clone 11 and the randomly chosen clones were all identical and 4 of the light chains of this set were also identical with one being dissimilar. This very limited diversity of binding sequences contrasts with the considerable diversity observed for HIV-1 gp120 binding clones identified from the same library although the donor's serum titers against gp120 and FG were similar. For instance, somatic variants of heavy and light chains were identified amongst the Fabs binding to gp120 whereas this was not the case here. This may reflect the chronic antigen stimulation in the case of HIV-1 gp120 compared to occasional stimulation in the case of RSV.

Competition ELISAs. Apparent binding affinities were estimated by competition of free FG-glycoprotein and FG coated on ELISA wells for Fab fragments as described (Zebedee, et al., Proc. Natl. Acad. Sci. USA, 89:3175, 1992).

Competition between Fab fragments and mouse monoclonal anti-F antibodies for coated FG was assessed essentially as described (Persson, et al., Proc. Natl. Acad. Sci. USA, 88:2432, 1991). These tests were performed in an attempt to identify the antigenic site on RSV F against which the Fabs were directed. RSV FG antigen was coated onto ELISA wells at 0.1 µg/ml overnight at 4° C. Wells were blocked, incubated with Fab supernates at 4× maximal binding level ($OD_{490}$=2.5, determined by indirect ELISA) for 1 hour at 37° C. and then incubated with mouse ascites fluid from one of 4 hybridoma cell lines producing RSV F-specific monoclonal antibodies (1142, 1153, 1112 or 1243;

Beeler, et al., *J. Virol.*, 63:2941, 1989) for 1 hour at 37° C. at a concentration to yield an $OD_{490}$=2.5. Wells were washed and developed with HRP-conjugated anti-mouse F(ab')$_2$. Percent inhibition was calculated as 100−([experimental OD/control OD (without initial competitor)]×100]. For the reciprocal assay, mouse antibody at a 4-fold excess was incubated with FG-coated plates at a 4-fold excess, and human Fab to yield an OD of 2.5 was added and detected with goat anti-human Fab.

The clone 11, 13 and 19 Fabs were further examined by inhibition ELISA which yielded apparent binding affinities of the order of $10^8 M^{-1}$. The ability of Fabs 11 and 13 and mouse monoclonal antibodies to compete for sites on FG was also investigated by competition ELISA. The mouse monoclonal antibodies used for this purpose define three sites on the F glycoprotein which appear important in neutralization. As shown in Table 5, the antibody against the B site competes with Fab 11, but there is little or no competition by the murine antibodies with Fab 13. This latter result may indicate affinity differences although little or no competition was observed when either Fab 13 or mouse mAb was used in excess. Alternative explanations are that the human neutralizing antibody response can be made, in part, against antigenic sites different from those seen by the mouse or that the result may reflect the smaller size of the Fab fragment since the three sites were defined using whole antibodies.

TABLE 5

INHIBITION OF HUMAN Fab BINDING TO
FG ANTIGEN BY MOUSE MONOCLONAL ANTIBODIES

| Mouse mAB | Antigenic Site | Percent Inhibition Fab 11 | Percent Inhibition Fab 13 |
|---|---|---|---|
| 1142 | A | 0.5 | 15.5 |
| 1153 | A | 0.0 | 19.3 |
| 1112 | B | 74.5 | 0.0 |
| 1243 | C | 0.0 | 13.9 |

The neutralizing activity of these Fabs was equivalent to that of a recently described humanized murine RSV F monoclonal antibody (Tempest, et al., *Bio/Technology*, 9:266, 1991) that was very active both in cell culture (0.4 μg per ml was sufficient to reduce virus plaques by 50%) and in mice (5 mg/kg was sufficient to reduce pulmonary virus titer by $10^5$ at the height of the infection). These monovalent Fabs of the present invention that lacked the Fc effector segment of a full length divalent IgG molecule were equivalent in neutralization function.

EXAMPLE 5

Generation of Recombinant Human Antibodies

The combinatorial phage library approach to immunoglobulin repertoire cloning made it recently possible to isolate gene fragments encoding human immunoglobulin G1 Fabs binding with high affinity to specific antigens (Barbas, et al., supra). The construction of genes encoding whole human anti-RSV antibodies based on one of these gene fragments and the efficient expression of these constructs by co-transfection of separate heavy and light chain vectors into a Chinese hamster ovary (CHO) cell line constitutively expressing a viral transactivator protein is possible as described below. This system is generally useful for the rapid analysis of recombinant antibodies derived from repertoire cloning.

Strains, plasmids and DNA manipulations. *E. coli* strain XL-1 blue (F) proAB, lacI$^q$ZDM15, Tn10(tet$^r$) (Stratagene) is used for all cloning experiments. Vectors pEE6hCMVneo, pEE6hCMVBgIII, a derivative of pEE6hCMV, and pE1001, are from Celltech Ltd., Slough UK.

DNA manipulations are performed according to standard technology (Sambrook, et al., supra), oligonucleotides are synthesized by b-cyanoethylphosphoramidite chemistry on an Applied Biosystems DNA synthesizer 380A and purified by denaturing PAGE. Restriction enzymes are from New England Biolabs. All constructs are verified by DNA-sequencing according to Sanger, supra.

Cell culture and DNA transfection. CHO L761h cells are grown in DMEM, 10% FCS, 1×NEAA (non-essential amino acids, GIBCO-BRL) and 2 mM glutamine. Transfection of DNA is done as previously described (Stephens, et al., *Nucl. Acids Res.*, 17:7110, 1989). For the selection of stable transfectants G418 (Geneticin, GIBCO-BRL) is added at 1 mg/ml. Cells are cloned by limiting dilution in 96 well microtitre plates.

Radioactive labeling of proteins and immunoprecipitation. The medium of transfected CHO cells in one well of a 24 well microtitre plate is replaced 24 hours after transfection with 1 ml DMEM (methionine-free), 10% FCS, 1×NEAA, 2 mM glutamine, 10 mM Na butyrate and 4.62 MBq Trans $S^{35}$ label (ICN Flow). After incubation for 3 days at 37° C., the culture supernatant is harvested by centrifugation at 14000 g for 5 minutes and stored at −20° C. until further examination. Tunicamycin is added when required at a final concentration of 10 mg/ml.

For the immunoprecipitation of IgG1, 200 ml of supernatant is mixed for two hours with preswollen protein A-Sepharose (Pharmacia), followed by centrifugation for 15 seconds at 7000 g and washing in lysis-buffer (10 mM Tris pH 7.4, 1 mM EDTA, 1% Nonidet P-40)/0.5 M NaCl. After two further washes in lysis buffer/0.1% SDS and 10 mM Tris pH 7.4/0.1% Nonidet P-40, the beads are extracted by boiling in reducing or non-reducing SDS-PAGE sample buffer and the supernatant from a centrifugation at 14000 g for 5 minutes is analyzed by SDS-PAGE on a 10% gel. After the run, the gel is soaked for 30 minutes in 1 M Na-salicylate, dried at 80° C. for two hours in a vacuum drier and exposed to an autoradiographic film at −70° C.

ELISAs. RSV antibody producing clones are detected using an ELISA 96 microtitre plate coated with 50 μl (0.1 mg) RSV-FG in PBS. Bound antibody was detected by anti-human kappa light chain peroxidase conjugate (Sigma, no. A7164). Binding affinities of antibodies and Fabs are estimated by competition ELISA.

The estimations of antibody amounts in CHO cell culture supernatants are performed by a competition ELISA on protein A coated microtitre plates. The standard curve is established by mixing a constant saturating amount of alkaline phosphatase labeled human IgG1 kappa (prepared according to Harlow and Lane, Antibodies: A Laboratory Manual, CSH Laboratory, CSH, NY, 1988) with varying amounts of human IgG1 kappa (Sigma, 13889) and measuring the protein A bound immunoglobulin alkaline phosphatase conjugate after washing with PBS.

Antibody purification and N-terminal sequencing. Antibodies are affinity purified on a Sepharose RSV-FG column prepared using cyanogen bromide-activated Sepharose (Sigma). The antibodies adsorbed to the beads are released by boiling in reducing sample buffer and heavy and light chains are separated by SDS-PAGE. For sequencing, proteins are blotted onto Immobilon membrane using 10 mM CAPS/10% MeOH as blotting buffer. Heavy and light chains are detected by PonceauS staining and sequenced by Edman degradation.

Design of the expression constructs. The concept is to generate separate vectors for the expression of heavy and light chains in CHO cells. As starting points, two derivatives of pEE6 (Whittle, et al., *Protein Engineering*, 1:499, 1987), in which transcription is driven by the human cytomegalovirus (hCMV) promoter/enhancer element are chosen. The Fab chosen to be expressed as a whole antibody is the high affinity RSV binder, clone 19, for example. For the secretory expression of the two immunoglobulins in CHO cells, the DNAs encoding light chain (LC) and Fd fragment of the heavy chain (HC) have to be combined with suitable signal peptides, which show a pronounced variety among immunoglobulins. From the DNA sequence it will be obvious which subgroup the Fd and LC of clone 19 belong to and therefore signal peptides from these gene families are chosen. Hence oligonucleotides encoding the HC signal peptide are synthesized according to the respective DNA sequence in the clones VH-26 (Matthysens, et al., In: Steinberg, C. and Lefkovits, I., eds., *The Immune System*, New York: S. Karger, 132, 1981) and those for the LC signal peptide are designed according to the leader peptide of the clone EVJK11 (Stavezner, et al., *Nucl. Acids Res.*, 13:3495, 1985). Due to the design of the *E. coli* expression vectors and the PCR primers, the first three (LC), and five (Fd) amino acids (aa) of the human immunoglobulins were not originally cloned. They were, therefore, included into the linkers encoding the signal peptides, according to the VH-26 and EVJK11 framework 1 (FR1) sequences. For the heavy chain vector it is possible to maintain the 5'XhoI cloning site, for the light chain construct; however, preservation of the Sacl site introduces a glutamic acid in position 3 of the mature protein rather than the glutamine found naturally. Further it creates a very unusual clustering of negative charges at the N-terminus in combination with the glutamic acid at +1 already present. Therefore, two different light chain constructs are made, on encoding glutamic acid and the other encoding the authentic glutamine at position +3, destroying the Sacl site used for cloning. To add the missing Fc part to the Fd, a corresponding DNA fragment is excised from plasmid pE1001, carrying a subclone of a genomic Ig gamma 1 clone (Takahashi, et al., *Cell*, 29-671, 1982). For the fusion of Fd and Fc a unique BstEII site in the DNA coding for the gamma 1 domain was used. To enable efficient translation initiation the natural Kozak sequences of the two signal peptides used were included in the design of the 5' ends of the linkers. The complete HC construct is cloned into the mammalian expression vector pEE6HCMVneo (Whittle, et al., supra) providing the hCMV promoter/enhancer element for transcription initiation, the SV40 signal for polyadenylation and the neomycin resistance gene, enabling the selection of stable transfectants (FIG. 5). The two LC constructs were each separately cloned into the vector pEE6hCMVBgIII (Stephens, et al., supra) which provides the same transcription regulatory signals but has no antibiotic resistance gene for selection in eukaryotic cells (FIG. 5). High level expression of Ig heavy chains alone is lethal for mammalian cells, therefore selection for the heavy chain vector coselects for the simultaneous synthesis of the light chain.

Transient expression in CHO-L761h cells. The development of the CHO cell line CHO L761h (Cockett, et al., *Nucl. Acids Res.*, 19:319, 1991), constitutively expressing a mutant adenovirus E1A gene which transactivates the hCMV promoter, allows sufficient expression levels for investigations with transiently transfected cells.

The immunoprecipitation by proteinA-Sepharose of radioactively labelled proteins from the culture supernatant of CHO L761h cells, transiently cotransfected with the LC and HC expression vectors, should reveal a band of about 150 kD, as expected for human IgGI under non-reducing SDS PAGE conditions.

Under reducing conditions these bands resolve into two proteins of about 50 and 25 kD, the molecular weights expected for Ig heavy and light chains. The kappa chain having two glutamic acids at the N-terminus migrates in the form of a broad band with the majority lagging behind the kappa chain with the natural glutamine containing N-terminus.

For the display of IgGl effector functions, it is important that the $C_H2$ domain is correctly N-glycosylated. In order to examine the glycosylation of the heavy chain, parallel transfections for subsequent cultivation in media with and without tunicamycin are performed. Corresponding immunoprecipitations should show that the heavy chain is N-glycosylated by CHO cells.

Secretion of IgG1/19 by stable transfected CHO cells. To examine the yield of antibody that can be produced by this system, stable transfectants are selected by the addition of G418 and subsequent limiting dilution of the cells. Clones are examined to show which cell lines produce detectable amounts of anti-RSV antibody. Of these, the highest producing clones are propagated for further analysis of productivity. The level of antibody secretion should be about 200-300 ng per ml in 24 hours from $2 \cdot 10^5$ cells.

Analysis of the secreted antibodies. Antibodies are purified by RSV affinity chromatography from culture supernatants and the first 5 N-terminal amino acids are determined by Edman degradation. For all antibody chains, correct and unambiguous processing by the signal peptidase should be shown with sequences obtained being exactly as predicted. The apparent binding affinities for RSV of the two antibodies are estimated by competitive ELISAs allowing comparison with that of the original Fab. Antibodies should bind RSV with an apparent affinity of about $10^8 M^{-1}$, typical for a high affinity antibody.

EXAMPLE 6

In Vivo Amelioration of RSV Infection Using Human Fab Monoclonal Antibody

Three Fabs were tested for therapeutic efficacy in mice infected with RSV. The RSV Fabs were produced as described above. RSV Fab 19 exhibited high neutralizing activity (titer 1552 at 258 µg/ml) against the virus when tested by the plaque reduction neutralization technique in HEp-2 cell cultures, whereas another RSV Fab 126 did not appear to possess neutralizing activity in cell culture. A third human monoclonal Fab directed against the envelope glycoprotein of the human immunodeficiency virus (HIV), studied as a control, did not exhibit neutralizing activity against RSV in cell culture. In an independent set of assays, the RSV Fab 19 was shown to also exhibit a very high fusion-inhibiting (FI) activity. The FI titer of the Fab 19 Fab was approximately one-third that of its neutralizing antibody titer.

Fifteen to thirty-two week old, female, Balb/c mice weighing on average 25 gms. were used. Mice were inoculated intranasally with $10^{6.3}$ plaque forming units (pfu) of RSV strain A2 contained in 100 µl of tissue culture medium. Inoculation was performed after mice had been anesthetized with methoxyflurane; under these conditions materials inoculated intranasally are delivered directly into the lungs. Six mice were included in each group studied. Three days after virus inoculation, 100 µl of Fab suspension was instilled intranasally under methoxyflurane anesthesia. Four days after virus inoculation the mice were sacrificed and their lungs were harvested (Murphy, et al., Vaccine, 8497-502, 1990 and Prince, et al., Am. J. Path., 93:771-792, 1978). Lung homogenates were titrated for RSV by plaque assay on HEp-2 cells maintained under semi-solid medium overlay at 37° C. in 5% $CO_2$ incubaubor (Prince, et al., 1978). Plaques were detected by the immunoperoxidase labeling procedure (Murphy, et al., 1990).

TABLE 6

EFFECT OF INTRANASALLY ADMINISTERED HUMAN RSV MONOCLONAL Fab 19 ON RSV INFECTION

| Fab administered on day 3 | Fab dose (mg/kg body weight) | Virus titer in lungs on day 4 | |
|---|---|---|---|
| | | RSV subgroup A* | Influenza** |
| RSV 19 | 0.516 | 2.4 +/− 0.33 | 6.4 +/− 0.25 |
| | 0.258 | 4.2 +/− 0.47 | n.d. |
| | 0.129 | 4.8 +/− 0.23 | n.d. |
| | 0.032 | 5.5 +/− 0.09 | n.d. |
| | 0.008 | 6.0 +/− 0.06 | n.d. |
| | 0.002 | 6.0 +/− 0.06 | n.d. |
| RSV 126 | 0.548 | 5.6 +/− 0.11 | 6.5 +/− 0.29 |
| | 0.274 | 5.9 +/− 0.12 | n.d. |
| | 0.137 | 5.9 +/− 0.10 | n.d. |
| | 0.034 | 6.0 +/− 0.08 | n.d. |
| | 0.009 | 6.2 +/− 0.09 | n.d. |
| | 0.002 | 5.9 +/− 0.06 | n.d |
| HIV DL 21 control | 0.600 | 5.9 +/− 0.04 | n.d. |
| | 0.300 | 5.9 +/− 0.14 | n.d. |
| None | n.a. | 6.1 +/− 0.14 | 6.8 +/− 0.08 |

*Animals were inoculated with $10^6$ p.f.u. intranasally on day 0. Titers calculated as $log_{10}$ pfu/g tissue (mean +/s.e. of 6 animals).
**Animals were inoculated with $10^6$ $TCID_{50}$ influenza A/Udorn intranasally on day 0. Titers calculated as $log_{10}$ $TCID_{50}$/g tissue (mean +/− s.e. of 4 animals).

As shown in Table 6, RSV Fab 19, that previously exhibited a high level of neutralizing activity in cell culture, was also effective in reducing the level of RSV in the lungs of Balb/c mice at the height of their RSV infection. As little as 3.2 µg of Fab 19 was active therapeutically in mice; this was the case in the mice given 129 µg of Fab 19 per kg body weight. Mice given 12.9 µg (or 516 µg per kg body weight) of Fab exhibited a more effective therapeutic result in which the titer of RSV in the lungs was reduced by a factor of 5000. In contrast, RSV Fab 126 or HIV Fab DL 21, which did not exhibit neutralizing activity against RSV in cell culture, also failed to reduce the titer of RSV in the lungs of infected mice. In addition, the RSV Fab 19 did not exhibit a therapeutic effect in mice infected with influenza A/Udorn/1972 virus providing additional evidence for the specificity of the therapeutic effect of this Fab against RSV infection in vivo (Table 6).

Next, the duration of the therapeutic effect of Fab 19 against RSV infection was investigated by measuring the amount of RSV present in the lungs of mice at various times after intranasal instillation of the Fab (Table 7).

TABLE 7

EFFECT OF SINGLE INTRANASAL DOSE THERAPY OF RSV-INFECTED Balb/c MICE WITH Fab 19

| Antibody used to treat on day 3* | Virus recovery from lungs ($log_{10}$ pfu/g tissue) | | | |
|---|---|---|---|---|
| | Day 4 | Day 6 | Day 8 | Day 10 |
| RSV Fab 19 | <1.7 | 4.8 +/− 0.18 | <1.7 | <1.7 |
| HIV Fab | 5.6 +/− 0.12 | 4.9 +/− 0.14 | <1.7 | <1.7 |
| JEC serum** | 4.8 +/− 0.10 | 4.3 +/− 0.21 | <1.7 | <1.7 |
| none | 5.8 +/− 0.07 | 5.1 +/− 0.09 | <1.7 | <1.7 |

*25 ug of indicated Fab or human RSV-immune serum at 1:4 dilution administered intranasally in 100 ul volume under light methoxyflurane anesthesia;
**JEC serum was human polyclonal immune serum with a 1:1782 titer of RSV neutralizing antibodies measured by plaque reduction against strain A2.

The ability of Fab 19 to cause a significant reduction in the amount of virus in the lungs 24 hours after treatment was confirmed. Importantly, the therapeutic effect of the clone Fab 19 was greater than that of the JEC human polyclonal serum which had a comparable neutralizing activity. However, two days later a rebound in virus titer was observed. Thus, on the third day post treatment (which was the sixth day post infection) the titer of pulmonary virus in the treated mice did not differ significantly from that of the control groups, namely mice given the HIV Fab or mice which did not receive any treatment.

These observations suggested that successful therapy with Fabs might require repeated administration in order to contain virus replication until recovery had occurred. The feasibility of this approach was investigated in a study summarized in Table 8.

TABLE 8

INCREASED THERAPEUTIC EFFECT OF RSV Fab 19 ON RSV INFECTION USING MULTIPLE ADMINISTRATIONS

| Treatment Group | Fab used to treat[a] | Day(s) on which treatment was given | Virus recovery from lungs ($log_{10}$ pfu/g tissue) | | | |
|---|---|---|---|---|---|---|
| | | | Day 4 | Day 5 | Day 6 | Day 7 |
| 1 | RSV Fab 19 | 3 | 3.1 +/− 0.25 | 4.0 +/− 0.41 | 4.3 +/− 0.34 | 4.2 +/− 0.10 |
| 2 | " | 3, 4 | n.d. | 2.4 +/− 0.15 | 3.8 +/− 0.12 | 3.3 +/− 0.15 |
| 3 | " | 3, 4, 5 | n.d. | n.d. | <1.7[b] | 2.0 +/− 0.19[c] |
| 4 | HIV Fab | 3, 4, 5 | n.d. | n.d. | 5.6 +/− 0.21 | 4.2 +/− 0.10 |
| 5 | none | — | 6.5 +/− 0.10 | 6.0 +/− 0.15 | 5.6 +/− 0.10 | 4.6 +/− 0.21 |

[a]25 ug of indicated Fab administered intranasally in a 100 ul volume under light methoxyflurane anesthesia.
[b]Virus was not recovered from any animal.
[c]Virus recovered from only 2 of 4 animals.
n.d. = not done.

One group of mice received RSV Fab 19 only on the third day post infection, another group was treated on the third and fourth days post infection, while the remaining group of mice received the Fab on the third, fourth and fifth days post infection. As in the prior experiments a single instillation of Fab 19 reduced pulmonary RSV in mice by a factor of 2500, but rebound to higher level occurred 24 hours later. Nonetheless, the titer of virus at that time, compared to the titer of the control mice, was still reduced by a factor of 100. During the next two days the titer of pulmonary virus never approached the high level that was present at the height of RSV replication, i.e., $10^{6.5}$ pfu on day 4 post infection. On the sixth and seventh day post infection the level of pulmonary virus remained at a level characteristic of imminent resolution of infection, namely $10^{4.2}$ to $10^{4.3}$ pfu which is similar to the seventh day post infection titer of the untreated group (Table 8).

Treatment on two successive days or three successive days caused an even greater reduction in pulmonary virus titer (Table 8). RSV could not be detected in the lungs of mice in the latter group one day after cessation of therapy, while a very modest rebound was observed one day later. This occurrence may not be significant because virus could only be detected in the lungs of 2 of 4 mice tested and the amount of virus recovered was still significantly less than the control group (Table 8). These observations suggest that RSV Fabs, such as Fab 19, would be effective for treatment of serious RSV lower respiratory tract disease in high risk infants and children as well as individuals of all ages who are immunodeficient, such as incident to genetic disease, suppressive therapy for organ transplantation or HIV infection. In addition, these observations suggest that direct respiratory tract administration of Fabs such as Fab 19 should also be elective for prophylaxis of serious RSV disease in high risk individuals who are exposed to infection during a hospital stay or a visit to an outpatient clinic.

These observations that demonstrated therapeutic activity of an antibody Fab fragment in vivo were completely unexpected because prior art had not taught or suggested these results. Indeed, to the best of the inventors knowledge, the in vivo therapeutic effect of antibody Fabs has not been reported previously. In fact, there are a number of theoretical considerations that make an in vivo therapeutic effect highly unlikely. Fabs are monovalent and thus can only attach to one site thereby precluding the cross linking of antigenic sites on separate virus particles. Because of this fact, cross linking by divalent antibody molecules or F(ab')$_2$s has been thought by many investigators to be a prerequisite for virus neutralization. Fabs would also be thought to be ineffective since Fabs lack the Fc portion of the immunoglobulin molecule which is responsible for many of the effector functions of antibodies, such as activation of the complement cascade and antibody dependent cell cytotoxicity (ADCC). Nevertheless, the RSV Fab 19 is very active in reducing the amount of virus present in RSV-infected lungs and, therefore, may signal the beginning of a new era of immunotherapy of mucosal virus infections, such as those caused by RSV as well as other respiratory tract viral pathogens such as the influenza viruses, the parainfluenza viruses, the rhinoviruses, and the coronaviruses whose growth in vivo is limited to the lumenal surface of the respiratory tract.

DEPOSIT OF MATERIALS

The following cell lines have been deposited on Sep. 15, 1992, with the American Type Culture Collection, 1301 Parklawn Drive, Rockville, Md., USA (ATCC).

| Cell Line | ATCC Accession No. |
|---|---|
| Clone 11 | ATCC 69071 |
| Clone 19 | ATCC 69072 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The organism will be made available by ATCC under the terms of the Budapest Treaty which assures permanent and unrestricted availability of the progeny of the culture to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and the Commissioner's rules pursuant thereto (including 37 CFR §1.14 with particular reference to 886 OG 638).

The assignee of the present application has agreed that if the culture deposit should die or be lost or destroyed when cultivated under suitable conditions, it will be promptly replaced on notification with a viable specimen of the same culture. Availability of the deposited strain is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the cell lines deposited, since the deposited embodiment is intended as a single illustration of one aspect of the invention and any cell lines that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents. Indeed, various modifications of the invention in addition to those shown and described herein will become apparent to those skilled in the art from the foregoing description and fall within the scope of the appended claims.

SUMMARY OF SEQUENCES

Sequence ID No. 1 is an amino acid sequence for a heavy chain of a human monoclonal antibody which neutralizes RSV;

Sequence ID No. 2 is an amino acid sequence for a heavy chain of a human monoclonal antibody which neutralizes RSV;

Sequence ID No. 3 is a polynucleotide sequence for production of an antibody heavy chain molecule;

Sequence ID No. 4 is a polynucleotide sequence for production of an antibody heavy chain molecule;

Sequence ID No. 5 is a polynucleotide sequence for production of an antibody heavy chain molecule;

Sequence ID No. 6 is a polynucleotide sequence for production of an antibody heavy chain molecule;

Sequence ID No. 7 is a polynucleotide sequence for production of an antibody heavy chain molecule;

Sequence ID No. 8 is a polynucleotide sequence for production of an antibody heavy chain molecule;

Sequence ID No. 9 is a polynucleotide sequence for production of an antibody heavy chain molecule;

Sequence ID No. 10 is a polynucleotide sequence for production of an antibody heavy chain molecule;

Sequence ID No. 11 is polynucleotide sequence for production of an antibody heavy chain molecule;

Sequence ID No. 12 polynucleotide sequence for production of an antibody heavy chain molecule;

Sequence ID No. 13 is a polynucleotide sequence for production of an antibody light chain molecule;

Sequence ID No. 14 is a polynucleotide sequence for production of an antibody light chain molecule;

Sequence ID No. 15 is a polynucleotide sequence for production of an antibody light chain molecule;

Sequence ID No. 16 is a polynucleotide sequence for production of an antibody light chain molecule;

Sequence ID No. 17 is a polynucleotide sequence for production of an antibody light chain molecule;

Sequence ID No. 18 is a polynucleotide sequence for production of an antibody light chain molecule;

Sequence ID No. 19 is a polynucleotide sequence for production of an antibody light chain molecule;

Sequence ID No. 20 is a polynucleotide sequence for production of an antibody light chain molecule;

Sequence ID No. 21 is an amino acid sequence for the heavy and light chain variable domains of Clones rsv 6H; 11H; 21H; 22H; and 23H (FIG. 4);

Sequence ID No. 22 is an amino acid sequence for the heavy and light chain variable domains of Clones rsv 13H and 19H (FIG. 4);

Sequence ID No. 23 is an amino acid sequence for the heavy and light chain variable domains of Clones rsv 6L; 11L; 21L; and 22L (FIG. 4);

Sequence ID No. 24 is an amino acid sequence for the heavy and light chain variable domains of Clone rsv 23L (FIG. 4);

Sequence ID No. 25 is an amino acid sequence for the heavy and light chain variable domains of Clones rsv 13L and 19L (FIG. 4);

Sequence ID No. 26 is a nucleotide sequence (and deduced amino acid sequence) of the light chain linker (FIG. 5, upper);

Sequence ID No. 27 is the deduced amino acid sequence of the light chain linker of Sequence ID No. 26 (FIG. 5);

Sequence ID No. 28 is a nucleotide sequence (and deduced amino acid sequence) of the heavy chain linker (FIG. 5, lower); and Sequence ID No. 29 is the deduced amino acid sequence of the heavy chain linker of Sequence ID No. 28 (FIG. 5).

The invention claimed is:

1. A method for providing passive immunotherapy to respiratory syncytial virus (RSV) disease in a host, comprising administering to the host an immunotherapeutically effective amount of 1) a human monoclonal antibody Fab fragment that neutralizes both antigenic subgroup A and subgroup B of respiratory syncytial virus (RSV), wherein the Fab fragment binds to an epitope present on glycoprotein F and is produced by clones having accession number ATCC 69071 or 2) a monoclonal antibody comprising said Fab fragment.

2. The method of claim 1, wherein the passive immunotherapy is provided prophylactically.

3. The method of claim 1, wherein the disease is selected from the group consisting of pneumonia and bronchiolitis.

4. The method of claim 1, wherein the administering is by the respiratory tract or parenterally.

5. The method of claim 4, wherein the respiratory tract administration is by pulmonary aerosol.

6. The method of claim 5, wherein the pulmonary aerosol comprises particles less than about 5 μm in diameter.

7. The method of claim 4 in which the material is administered as a liquid.

8. The method of claim 7, wherein the liquid is administered using a bronchoscope or artificial airway.

9. The method of claim 4, wherein the parenteral administration is by subcutaneous, intramuscular, intraperitoneal, intracavity, transdermal, or intravenous injection.

10. The method of claim 4, wherein the parenteral administration is a gradual perfusion.

11. The method of claim 10, wherein the gradual perfusion is by intravenous or peristaltic means.

12. The method of claim 1, wherein the immunotherapeutically effective amount is from about 0.01 mg/kg to about 300 mg/kg.

13. The method of claim 1, wherein the immunotherapeutically effective amount is from about 0.1 mg/kg to about 200 mg/kg.

14. The method of claim 1, wherein the immunotherapeutically effective amount is from about 0.2 mg/kg to about 20 mg/kg.

15. The method of claim 1, wherein the host is a human.

16. The method of claim 1, wherein the Fab fragment comprises a heavy chain comprising the polypeptide sequence

```
(SEQ. I.D. 2)
HLPDYWNLDYTRFFYYMDV.
```

* * * * *

```
                       SEQUENCE LISTING

<160> NUMBER OF SEQ ID NOS: 37

<210> SEQ ID NO 1
<211> LENGTH: 10
<212> TYPE: PRT
<213> ORGANISM: Homo sapiens

<400> SEQUENCE: 1

Ala Pro Ile Ala Pro Pro Tyr Phe Asp His
1               5                   10

<210> SEQ ID NO 2
<211> LENGTH: 16
<212> TYPE: PRT
<213> ORGANISM: Homo sapiens

<400> SEQUENCE: 2

His Leu Pro Asp Tyr Trp Asn Leu Asp Tyr Thr Arg Phe Phe Tyr Tyr
1               5                   10                  15

<210> SEQ ID NO 3
<211> LENGTH: 32
<212> TYPE: DNA
<213> ORGANISM: Artificial Sequence
<220> FEATURE:
<223> OTHER INFORMATION: Synthetically generated primer

<400> SEQUENCE: 3
```
ggccgcaaat tctatttcaa ggagacagtc at                                    32

<210> SEQ ID NO 4
<211> LENGTH: 36
<212> TYPE: DNA
<213> ORGANISM: Artificial Sequence
<220> FEATURE:
<223> OTHER INFORMATION: Synthetically generated primer

<400> SEQUENCE: 4
aatgaaatac ctattgccta cggcagccgc tggatt                                36

<210> SEQ ID NO 5
<211> LENGTH: 32
<212> TYPE: DNA
<213> ORGANISM: Artificial Sequence
<220> FEATURE:
<223> OTHER INFORMATION: Synthetically generated primer

<400> SEQUENCE: 5
gttattactc gctgcccaac cagccatggc cc                                    32

<210> SEQ ID NO 6
<211> LENGTH: 29
<212> TYPE: DNA
<213> ORGANISM: Artificial Sequence
<220> FEATURE:
<223> OTHER INFORMATION: Synthetically generated primer

<400> SEQUENCE: 6
cagtttcacc tgggccatgg ctggttggg                                        29

<210> SEQ ID NO 7
<211> LENGTH: 40
<212> TYPE: DNA
<213> ORGANISM: Artificial Sequence
<220> FEATURE:
<223> OTHER INFORMATION: Synthetically generated primer

<400> SEQUENCE: 7
cagcgagtaa taacaatcca gcggctgccg taggcaatag                            40

<210> SEQ ID NO 8
<211> LENGTH: 38
<212> TYPE: DNA
<213> ORGANISM: Artificial Sequence
<220> FEATURE:
<223> OTHER INFORMATION: Synthetically generated primer

<400> SEQUENCE: 8
gtatttcatt atgactgtct ccttgaaata gaatttgc                              38

<210> SEQ ID NO 9
<211> LENGTH: 40
<212> TYPE: DNA
<213> ORGANISM: Artificial Sequence
<220> FEATURE:
<223> OTHER INFORMATION: Synthetically generated primer

<400> SEQUENCE: 9
aggtgaaact gctcgagatt tctagactag ttacccgtac                            40

<210> SEQ ID NO 10
<211> LENGTH: 38
<212> TYPE: DNA

```
<213> ORGANISM: Artificial Sequence
<220> FEATURE:
<223> OTHER INFORMATION: Synthetically generated primer

<400> SEQUENCE: 10
cggaacgtcg tacgggtaac tagtctagaa atctcgag                              38

<210> SEQ ID NO 11
<211> LENGTH: 33
<212> TYPE: DNA
<213> ORGANISM: Artificial Sequence
<220> FEATURE:
<223> OTHER INFORMATION: Synthetically generated primer

<400> SEQUENCE: 11
gacgttccgg actacggttc ttaatagaat tcg                                   33

<210> SEQ ID NO 12
<211> LENGTH: 28
<212> TYPE: DNA
<213> ORGANISM: Artificial Sequence
<220> FEATURE:
<223> OTHER INFORMATION: Synthetically generated primer

<400> SEQUENCE: 12
tcgacgaatt ctattaagaa ccgtagtc                                         28

<210> SEQ ID NO 13
<211> LENGTH: 34
<212> TYPE: DNA
<213> ORGANISM: Artificial Sequence
<220> FEATURE:
<223> OTHER INFORMATION: Synthetically generated primer

<400> SEQUENCE: 13
tgaattctaa actagtcgcc aaggagacag tcat                                  34

<210> SEQ ID NO 14
<211> LENGTH: 36
<212> TYPE: DNA
<213> ORGANISM: Artificial Sequence
<220> FEATURE:
<223> OTHER INFORMATION: Synthetically generated primer

<400> SEQUENCE: 14
aatgaaatac ctattgccta cggcagccgc tggatt                                36

<210> SEQ ID NO 15
<211> LENGTH: 31
<212> TYPE: DNA
<213> ORGANISM: Artificial Sequence
<220> FEATURE:
<223> OTHER INFORMATION: Synthetically generated primer

<400> SEQUENCE: 15
gttattactc gctgcccaac cagccatggc c                                     31

<210> SEQ ID NO 16
<211> LENGTH: 30
<212> TYPE: DNA
<213> ORGANISM: Artificial Sequence
<220> FEATURE:
<223> OTHER INFORMATION: Synthetically generated primer

<400> SEQUENCE: 16
gagctcgtca gttctagagt taagcggccg                                       30
```

```
<210> SEQ ID NO 17
<211> LENGTH: 48
<212> TYPE: DNA
<213> ORGANISM: Artificial Sequence
<220> FEATURE:
<223> OTHER INFORMATION: Synthetically generated primer

<400> SEQUENCE: 17
ctatttcatt atgactgtct ccttggcgac tagtttagaa ttcaagct                    48

<210> SEQ ID NO 18
<211> LENGTH: 40
<212> TYPE: DNA
<213> ORGANISM: Artificial Sequence
<220> FEATURE:
<223> OTHER INFORMATION: Synthetically generated primer

<400> SEQUENCE: 18
cagcgagtaa taacaatcca gcggctgccg taggcaatag                             40

<210> SEQ ID NO 19
<211> LENGTH: 27
<212> TYPE: DNA
<213> ORGANISM: Artificial Sequence
<220> FEATURE:
<223> OTHER INFORMATION: Synthetically generated primer

<400> SEQUENCE: 19
tgacgagctc ggccatggct ggttggg                                           27

<210> SEQ ID NO 20
<211> LENGTH: 24
<212> TYPE: DNA
<213> ORGANISM: Artificial Sequence
<220> FEATURE:
<223> OTHER INFORMATION: Synthetically generated primer

<400> SEQUENCE: 20
tcgacggccg cttaactcta gaac                                              24

<210> SEQ ID NO 21
<211> LENGTH: 129
<212> TYPE: PRT
<213> ORGANISM: Homo sapiens

<400> SEQUENCE: 21

Gln Val Lys Leu Leu Glu Gln Ser Gly Gly Gly Leu Val Gln Pro Gly
  1               5                  10                  15

Gly Ser Leu Arg Leu Ser Cys Ala Val Ser Gly Val Thr Phe Ser Ala
             20                  25                  30

Tyr Ala Met Ser Trp Val Arg Gln Ala Pro Gly Lys Gly Leu Glu Trp
         35                  40                  45

Val Ser Gly Ile Ser Gly Ser Gly Asp Ser Thr Asp Tyr Ala Asp Ser
     50                  55                  60

Val Lys Gly Arg Leu Thr Ile Ser Arg Asp Asn Ser Lys Asn Thr Leu
 65                  70                  75                  80

Tyr Leu Gln Met Asn Ser Leu Arg Ala Glu Asp Thr Ala Ile Tyr Tyr
                 85                  90                  95

Cys Ala Ser His Leu Pro Asp Tyr Trp Asn Leu Asp Tyr Thr Arg Phe
            100                 105                 110

Phe Tyr Tyr Met Asp Val Trp Gly Lys Gly Thr Thr Val Thr Val Ser
```

-continued

```
                115                 120                 125
Ser

<210> SEQ ID NO 22
<211> LENGTH: 120
<212> TYPE: PRT
<213> ORGANISM: Homo sapiens

<400> SEQUENCE: 22

Gln Val Lys Leu Leu Glu Ser Gly Gly Gly Leu Val Arg Leu Ala
  1               5                  10                  15

Gly Ser Leu Arg Leu Ser Cys Ala Ala Ser Gly Thr Thr Leu Ser Gly
                 20                  25                  30

Tyr Thr Met His Trp Val Arg Gln Ala Pro Gly Lys Gly Leu Glu Trp
                 35                  40                  45

Val Ser Ser Ile Thr Gly Gly Ser Asn Phe Ile Asn Tyr Ser Asp Ser
                 50                  55                  60

Val Lys Gly Arg Phe Thr Ile Ser Arg Asp Asn Ala Lys Asn Ser Leu
 65                  70                  75                  80

Tyr Leu Gln Met Asn Ser Leu Thr Ala Glu Asp Thr Ala Val Tyr Tyr
                 85                  90                  95

Cys Ala Thr Ala Pro Ile Ala Pro Pro Tyr Phe Asp His Trp Gly Gln
                100                 105                 110

Gly Thr Leu Val Thr Val Ser Ser
                115                 120

<210> SEQ ID NO 23
<211> LENGTH: 109
<212> TYPE: PRT
<213> ORGANISM: Homo sapiens

<400> SEQUENCE: 23

Met Ala Glu Leu Thr Gln Ser Pro Gly Thr Leu Ser Leu Ser Pro Gly
  1               5                  10                  15

Glu Arg Ala Thr Leu Ser Cys Arg Ala Thr Gln Ser Ile Ser Ser Asn
                 20                  25                  30

Tyr Leu Ala Trp Tyr Gln Gln Arg Pro Gly Gln Ala Pro Arg Leu Leu
                 35                  40                  45

Ile Tyr Gly Ala Ser Asn Arg Ala Thr Asp Ile Pro Asp Arg Phe Ser
                 50                  55                  60

Gly Ser Gly Ser Gly Thr Asp Phe Thr Leu Thr Ile Ser Arg Leu Glu
 65                  70                  75                  80

Pro Glu Asp Phe Ala Met Tyr Tyr Cys Gln Gln Tyr Asp Ile Ser Pro
                 85                  90                  95

Tyr Thr Phe Gly Gln Gly Thr Lys Leu Glu Ile Lys Arg
                100                 105

<210> SEQ ID NO 24
<211> LENGTH: 109
<212> TYPE: PRT
<213> ORGANISM: Homo sapiens

<400> SEQUENCE: 24

Met Ala Glu Leu Thr Gln Ser Pro Val Thr Leu Ser Val Ser Pro Gly
  1               5                  10                  15

Glu Arg Val Ala Leu Ser Cys Lys Ala Ser Gln Asn Ile Asn Asp Asn
                 20                  25                  30
```

```
Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
        50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Gly Ser Pro Tyr
                85                  90                  95

Thr Phe Gly Gln Gly Thr Lys Leu Glu Ile Lys Arg Thr
                100                 105

<210> SEQ ID NO 25
<211> LENGTH: 108
<212> TYPE: PRT
<213> ORGANISM: Homo sapiens

<400> SEQUENCE: 25

Met Ala Glu Leu Thr Gln Ser Pro Ser Ser Leu Ser Ala Ser Val Gly
1               5                   10                  15

Asp Arg Val Thr Ile Thr Cys Arg Ala Thr Gln Ser Val Ser Asn Phe
            20                  25                  30

Leu Asn Trp Tyr Gln Gln Lys Pro Gly Glu Ala Pro Thr Leu Leu Ile
            35                  40                  45

Tyr Asp Ala Ser Thr Ser Gln Ser Gly Val Pro Ser Arg Phe Ser Gly
        50                  55                  60

Ser Gly Ser Gly Met Asp Phe Ser Leu Thr Ile Ser Ser Leu Gln Pro
65                  70                  75                  80

Glu Asp Leu Ala Met Tyr Tyr Cys Gln Ala Ser Ile Asn Thr Pro Leu
                85                  90                  95

Phe Gly Gly Gly Thr Arg Ile Asp Met Arg Arg Thr
                100                 105

<210> SEQ ID NO 26
<211> LENGTH: 86
<212> TYPE: DNA
<213> ORGANISM: Homo sapiens
<220> FEATURE:
<221> NAME/KEY: CDS
<222> LOCATION: (15)...(86)

<400> SEQUENCE: 26
aagcttaggg aacc atg gaa acc cca gcg cag ctt ctc ttc ctc ctg cta      50
                Met Glu Thr Pro Ala Gln Leu Leu Phe Leu Leu Leu
                1               5                   10 ctc tgg ctc cca gat acc acc gga gaa att sag ctc                       86
Leu Trp Leu Pro Asp Thr Thr Gly Glu Ile Xaa Leu
        15                  20

<210> SEQ ID NO 27
<211> LENGTH: 24
<212> TYPE: PRT
<213> ORGANISM: Homo sapiens
<220> FEATURE:
<221> NAME/KEY: VARIANT
<222> LOCATION: 23
<223> OTHER INFORMATION: Xaa = Gln, or Glu

<400> SEQUENCE: 27

Met Glu Thr Pro Ala Gln Leu Leu Phe Leu Leu Leu Trp Leu Pro
1               5                   10                  15

Asp Thr Thr Gly Glu Ile Xaa Leu
            20
```

```
<210> SEQ ID NO 28
<211> LENGTH: 89
<212> TYPE: DNA
<213> ORGANISM: Homo sapiens
<220> FEATURE:
<221> NAME/KEY: CDS
<222> LOCATION: (15)...(89)

<400> SEQUENCE: 28
aagcttaact cacc atg gag ttt ggg ctg agc tgg ctt ttt ctt gtg gct         50
               Met Glu Phe Gly Leu Ser Trp Leu Phe Leu Val Ala
                 1               5                  10 att tta aaa ggt gtc cag tct gag gtg gag ctg ctc gag                     89
Ile Leu Lys Gly Val Gln Ser Glu Val Glu Leu Leu Glu
        15                  20                  25

<210> SEQ ID NO 29
<211> LENGTH: 25
<212> TYPE: PRT
<213> ORGANISM: Homo sapiens

<400> SEQUENCE: 29

Met Glu Phe Gly Leu Ser Trp Leu Phe Leu Val Ala Ile Leu Lys Gly
  1               5                  10                  15

Val Gln Ser Glu Val Glu Leu Leu Glu
            20                  25

<210> SEQ ID NO 30
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 30
gtcgttgacc aggcagccca g                                                 21

<210> SEQ ID NO 31
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 31
atagaagttg ttcagcaggc a                                                 21

<210> SEQ ID NO 32
<211> LENGTH: 17
<212> TYPE: DNA
<213> ORGANISM: Artificial Sequence
<220> FEATURE:
<223> OTHER INFORMATION: Synthetically generated primer

<400> SEQUENCE: 32
attaaccctc actaaag                                                      17

<210> SEQ ID NO 33
<211> LENGTH: 22
<212> TYPE: DNA
<213> ORGANISM: Artificial Sequence
<220> FEATURE:
<223> OTHER INFORMATION: Synthetically generated primer
```

```
<400> SEQUENCE: 33
gaattctaaa ctagctagtt cg                                                    22

<210> SEQ ID NO 34
<211> LENGTH: 36
<212> TYPE: PRT
<213> ORGANISM: Homo sapiens

<400> SEQUENCE: 34

Met Lys Tyr Leu Leu Pro Thr Ala Ala Ala Gly Leu Leu Leu Leu Ala
 1               5                  10                  15

Ala Gln Pro Ala Met Ala Gln Val Lys Leu Tyr Pro Tyr Asp Val Pro
            20                  25                  30

Asp Tyr Ala Ser
        35

<210> SEQ ID NO 35
<211> LENGTH: 23
<212> TYPE: PRT
<213> ORGANISM: Homo sapiens

<400> SEQUENCE: 35

Met Lys Tyr Leu Leu Pro Thr Ala Ala Ala Gly Leu Leu Leu Leu Ala
 1               5                  10                  15

Ala Gln Pro Ala Met Ala Glu
            20

<210> SEQ ID NO 36
<211> LENGTH: 86
<212> TYPE: DNA
<213> ORGANISM: Homo sapiens

<400> SEQUENCE: 36
gagctsaatt tctccggtgg tatctgggag ccagagtagc aggaggaaga gaagctgcgc           60
tggggtttcc atggttccct aagctt                                               86

<210> SEQ ID NO 37
<211> LENGTH: 89
<212> TYPE: DNA
<213> ORGANISM: Homo sapiens

<400> SEQUENCE: 37
ctcgagcagc tccacctcag actggacacc ttttaaaata gccacaagaa aaagccagct           60
cagcccaaac tccatggtga gttaagctt                                            89
```